(12) United States Patent
Verkruijsse et al.

(10) Patent No.: US 11,202,582 B2
(45) Date of Patent: Dec. 21, 2021

(54) DEVICE FOR USE IN BLOOD OXYGEN SATURATION MEASUREMENT

(71) Applicant: KONINKLIJKE PHILIPS N.V., Eindhoven (NL)

(72) Inventors: Willem Verkruijsse, Veldhoven (NL); Simone Cornelia Maria Anna Ordelman, S-Hertogenbosch (NL); Cristian Nicolae Presura, Veldhoven (NL); Rick Bezemer, Amsterdam (NL); Calina Ciuhu, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 367 days.

(21) Appl. No.: 16/323,560

(22) PCT Filed: Aug. 7, 2017

(86) PCT No.: PCT/EP2017/069883
§ 371 (c)(1),
(2) Date: Feb. 6, 2019

(87) PCT Pub. No.: WO2018/029123
PCT Pub. Date: Feb. 15, 2018

(65) Prior Publication Data
US 2019/0167124 A1 Jun. 6, 2019

Related U.S. Application Data

(60) Provisional application No. 62/372,376, filed on Aug. 9, 2016.

(30) Foreign Application Priority Data

Aug. 9, 2016 (EP) ..................................... 16183404

(51) Int. Cl.
*A61B 5/1455* (2006.01)
*A61B 5/026* (2006.01)
*A61B 5/00* (2006.01)

(52) U.S. Cl.
CPC ........ *A61B 5/0261* (2013.01); *A61B 5/14552* (2013.01); *A61B 5/6826* (2013.01);
(Continued)

(58) Field of Classification Search
CPC ... A61B 5/1455; A61B 5/0261; A61B 5/7221; A61B 5/7278; A61B 5/6826; A61B 5/14552
See application file for complete search history.

(56) References Cited

U.S. PATENT DOCUMENTS 6,763,256 B2 * 7/2004 Kimball ................. A61B 5/721
600/336
7,254,429 B2 8/2007 Schurman
(Continued)

FOREIGN PATENT DOCUMENTS

EP 0983017 3/2000
WO 2013/030744 3/2013

OTHER PUBLICATIONS

Jakovels, et al: "LASCA and PPG imaging for non-contact assessment of skin blood supply". SPIE-International Society for Optical Engineering. Proceedings, vol. 8668, Mar. 6, 2013.
(Continued)

*Primary Examiner* — Eric F Winakur

(57) ABSTRACT

The present invention relates to a device (10), system (1) and method (200) for use in blood oxygen saturation measurement of a subject. To enable blood oxygen saturation measurements with improved reliability, a processing device (10) is presented comprising an input (11) for receiving first
(Continued)

and second detection data of a tissue region of the subject, said first detection data being data acquired over time by detecting radiation at a first wavelength (λ1) and at a second wavelength (λ2) received from said tissue region; said second detection data being data acquired over time by detecting radiation at the first wavelength and at the second wavelength received from said tissue region in response to coherent light at the first wavelength and coherent light at the second wavelength being emitted towards the tissue region; a PPG unit (12) for deriving, from said first detection data, a first PPG signal indicative of an absorption of light within the tissue region at the first wavelength, and a second PPG signal indicative of an absorption of light within the tissue region at the second wavelength; a flow unit (13) for deriving, from said second detection data, a first flow signal indicative of a flow of light scattering particles within the tissue region probed at the first wavelength, and a second flow signal indicative of a flow of light scattering particles within the tissue region probed at the second wavelength; and a processing unit (14) for correcting said PPG signals based on said flow signals and/or for providing a feedback signal based on a comparison of the first and second flow signals.

15 Claims, 10 Drawing Sheets

(52) U.S. Cl.
CPC .......... *A61B 5/7221* (2013.01); *A61B 5/7278* (2013.01); *A61B 2560/0223* (2013.01); *A61B 2562/0238* (2013.01); *A61B 2562/0242* (2013.01)

(56) References Cited

U.S. PATENT DOCUMENTS

| | | | |
|---|---|---|---|
| 8,417,307 B2* | 4/2013 | Presura | A61B 5/14551 600/324 |
| 9,385,768 B2 | 7/2016 | De Haan | |
| 9,730,622 B2 | 8/2017 | Eisen | |
| 2008/0103378 A1 | 5/2008 | Kimball | |
| 2010/0240973 A1 | 9/2010 | Presura | |
| 2011/0082355 A1 | 4/2011 | Eisen | |
| 2015/0105638 A1 | 4/2015 | Eisen | |
| 2017/0127981 A1 | 5/2017 | Vermeulen | |

OTHER PUBLICATIONS

Allen et al: "Microvascular imaging: techniques and opportunities for clinical physiological measurements". Physiological Measurement, Institute of Physics Publishing, Bristol, GB, vol. 35, No. 7, Jun. 9, 2014.

Spigulis et al: "Multi-wavelengt photoplethysmography for simultaneous recording of skin blood pulsations at different vascular depths". SPIE—International Society for Optical Engineering. Proceedings, vol. 6430, Feb. 1, 2007.

Das, et al: "Pulse oximeter accuracy and precision at five different sensor locations in infants and children with cyanotic heart disease", Indian Journal of Anesthesia, 54(6):531-534, 2010.

Kong, et al: "Non-contact detection of oxygen saturalion based on visible light imaging device using ambient light", Optics Express 21:17464, 2013.

Wieringa, et al.: "Contactless multiple wavelength photoplethysmographic imaging: a first step toward "SpO2 camera" technology," Ann. Biomed. Eng. 33, 1034-1041, 2005.

Verkruysse, et al: "Calibration of Contactless Pulse Oximetry", Anesthesia & Analgesia, 2016.

Dicristina, et al: "Improve Sensor Performance and SNR in Pulse Oximeter Designs", Jun. 21, 2010 https://www.maximintegrated.com/en/app-notes/index.mvp/id/4671#.

Bratchenia, et al: "Millimeter-resolution acousto-optic quantitative imaging in a tissue model system", Journal of Biomedical Optics 14(3), 034031 (May/Jun. 2009).

Stuban, et al: "Non-invasive calibration method for pulse oximeters", Electrical Engineering 52/1-2 (2008) 91-94.

* cited by examiner

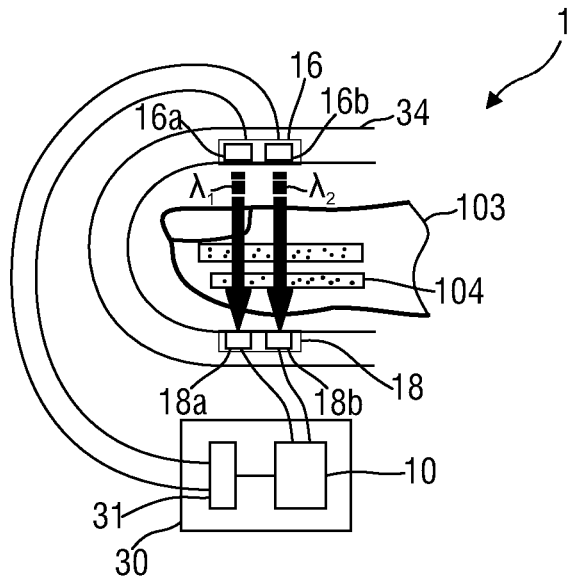
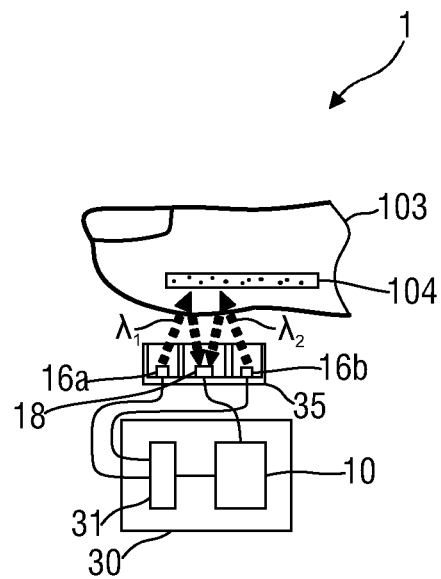
FIG.3         FIG.4
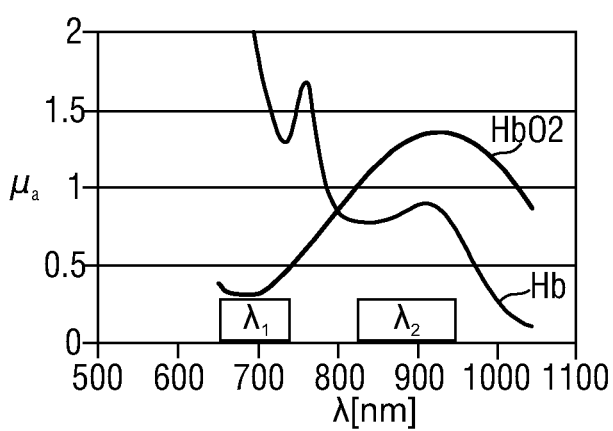
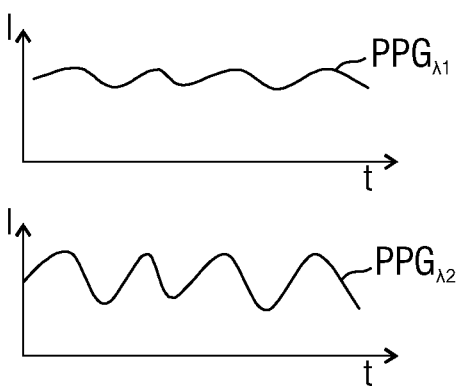
FIG.5A        FIG.5B

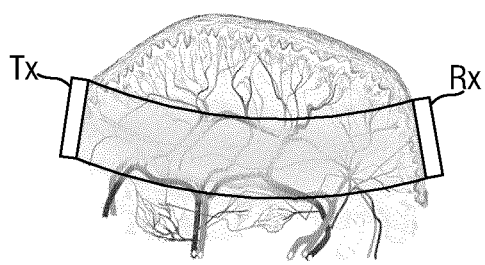
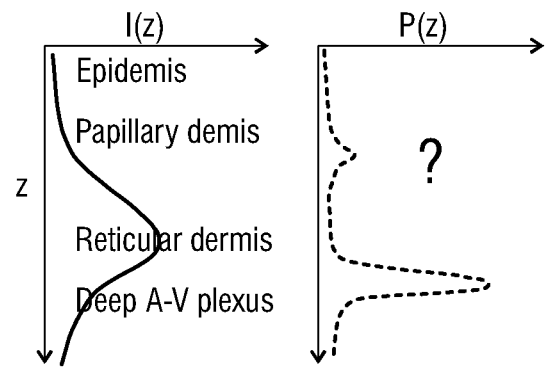
FIG.6A  FIG.6B  FIG.6C
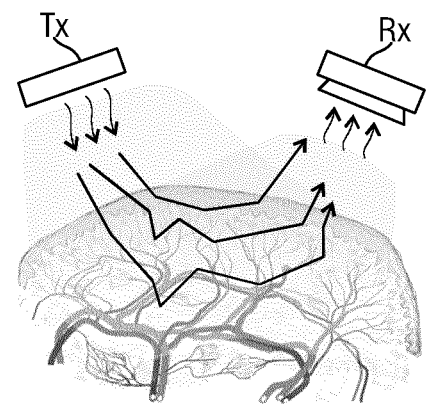
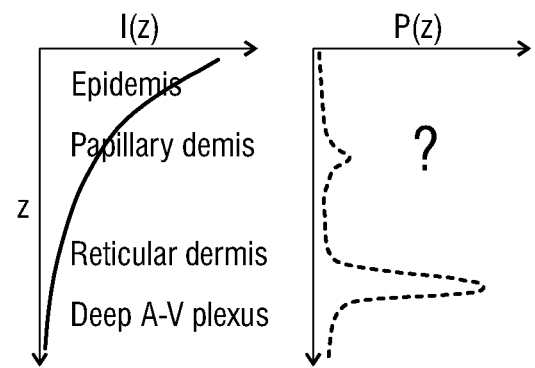
FIG.7A  FIG.7B  FIG.7C

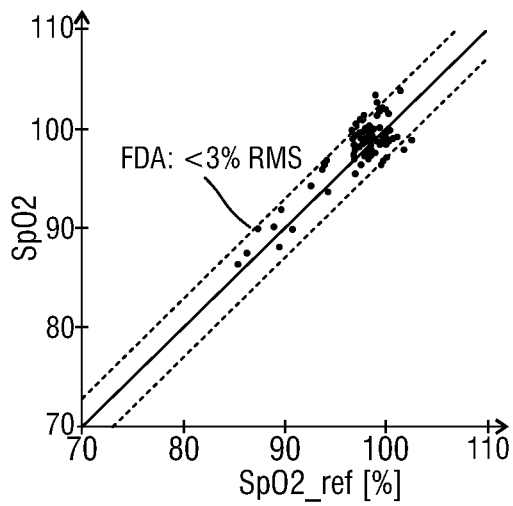
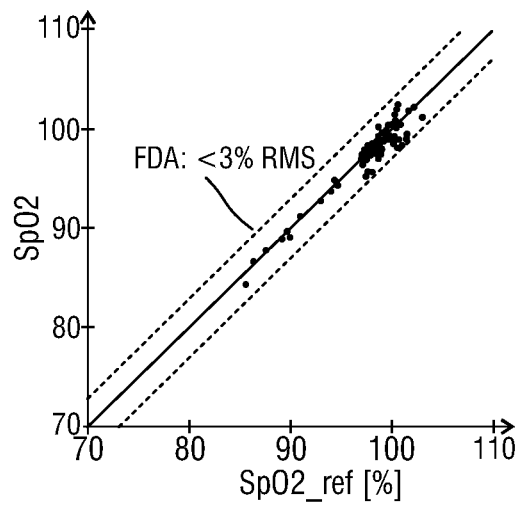
FIG.8A  FIG.8B
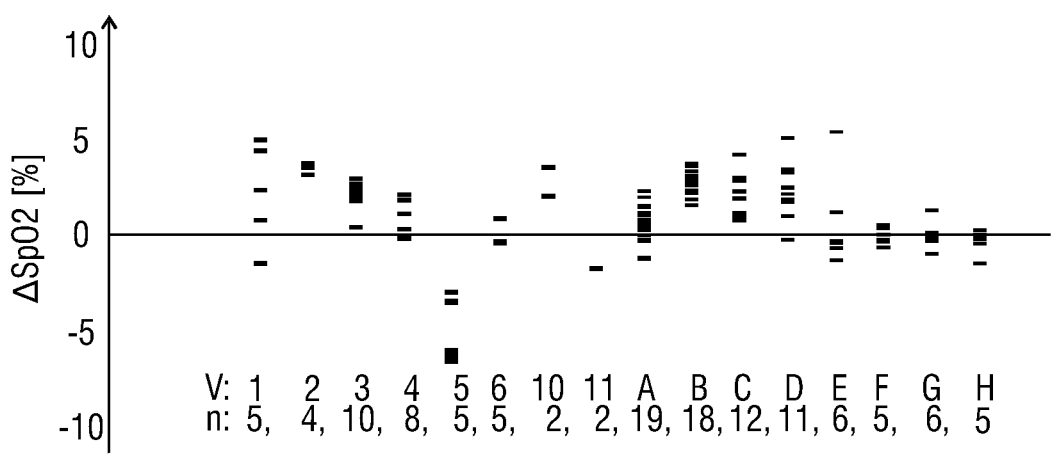
FIG.9

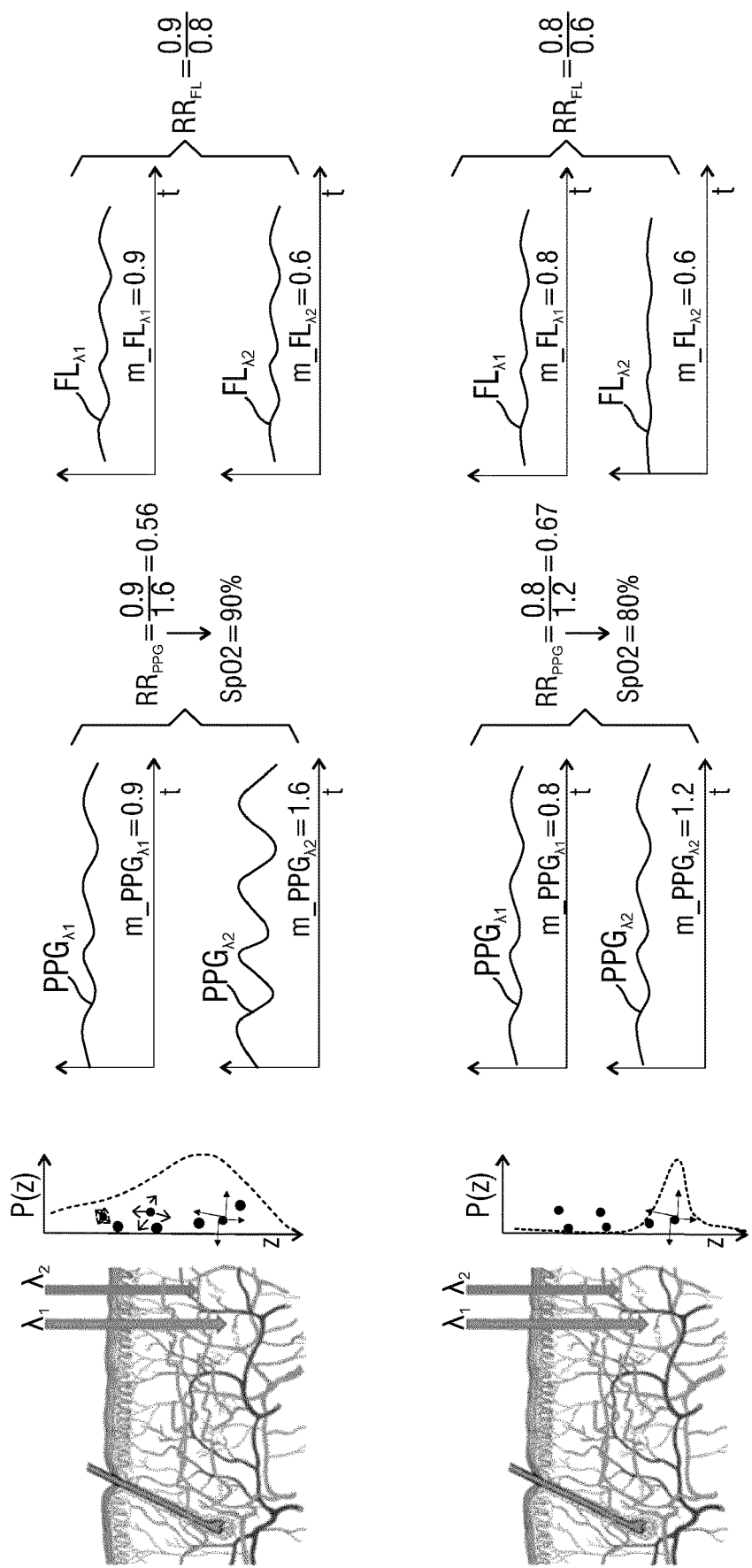

DEVICE FOR USE IN BLOOD OXYGEN SATURATION MEASUREMENT

CROSS REFERENCE TO RELATED APPLICATIONS

This application is the U.S. National Phase application under 35 U.S.C. § 371 of International Application No. PCT/EP2017/069883 filed Aug. 7, 2017, published as WO 2018/029123 on Feb. 15, 2018, which claims the benefit of European Patent Application Number 16183404.9 filed Aug. 9, 2016 and U.S. Provisional Patent Application No. 62/372,376 filed Aug. 9, 2016. These applications are hereby incorporated by reference herein.

FIELD OF THE INVENTION

The present invention relates to the field of medical technology, and in particular to a processing device, system and method for use in blood oxygen saturation measurement of a subject. The present invention further relates to a corresponding computer program for carrying out said method.

BACKGROUND OF THE INVENTION

Vital signs of a person, for example the heart rate (HR), the respiration rate (RR) or the blood oxygen saturation, serve as indicators of the current state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant pulsatile change of light absorption of a tissue region or volume of interest. Besides information about the heart rate, a PPG waveform can comprise information attributable to further physiological phenomena such as the respiration. By evaluating the absorption at different wavelengths (typically red and infrared), the blood oxygen saturation can be determined. This is due to the fact that oxygenated hemoglobin ($HbO_2$) and reduced hemoglobin (Hb) show a different absorption spectrum. The blood color thus depends on the blood oxygen saturation.

Conventional pulse oximeters for measuring the heart rate and the oxygen saturation of a subject are attached to a skin of the subject, for instance to a fingertip, earlobe or forehead. Therefore, they are referred to as 'contact' PPG devices. A typical pulse oximeter comprises a red LED and an infrared LED as light sources and one photodiode for detecting light that has been transmitted through patient tissue. Commercially available pulse oximeters quickly switch between measurements at a red and an infrared wavelength and thereby measure the transmissivity of the same area or volume of tissue at two different wavelengths. This is referred to as time-division-multiplexing. The pulsatile absorption at the first and at the second wavelength leads to a first PPG signal indicative of an absorption of light within the tissue region at the first wavelength, and a second PPG signal indicative of an absorption of light within the tissue region at the second wavelength. The arterial oxygen saturation (SpO2) can estimated from a relative pulsatile amplitude at the different wavelengths.

A problem involved with conventional pulse oximetry (POX) is the limited accuracy, typically ±3 saturation percent. While such an accuracy is generally acceptable for adults, a higher accuracy would be desirable for neonate patients in a neonate intensive care unit (NICU) because a target range for the blood oxygen saturation may be 91%-95%. Too low oxygen saturation can lead to undersupply, whereas a too high oxygen saturation can lead to blindness of neonates. In particularly critical patients, the target range can be controlled by a measurement of the fraction of inspired oxygen ($FiO_2$) or based on blood samples.

A further problem in the context of conventional pulse oximetry is alarm fatigue. Alarm fatigue occurs when one is exposed to a large number of frequent alarms and consequently becomes desensitized to them. Desensitization can lead to longer response time or to missing important alarms. For a target blood oxygen saturation range in a NICU of 91%-95%, alarm thresholds may be set at 89% and 95%. Hence, in view of the limited accuracy of 3 saturation percent, there is a high risk of false alarms. It would thus be advantageous to improve the accuracy to reduce false alarms and alarm fatigue.

A simple, yet effective solution to improve the accuracy is carefully selecting the location on the body of the subject where the pulse oximeter is placed, as described in Das et al., "Pulse oximeter accuracy and precision at five different sensor locations in infants and children with cyanotic heart disease", Indian Journal of Anesthesia, 54(6):531-534, 2010. It has been found that the highest accuracy can be achieved with a sole sensor.

WO 2013/030744 A1 discloses a wearable pulse oximetry device. The pulse oximetry device is mounted on a wrist strap and fixates an area above a distal end of the ulna with a domed-shaped structure. This area is used as the measuring area. The measurement is carried out by a detector positioned above the fixated area that detects light emitted by light sources having different wavelengths that are located at a periphery of the fixated area. Hence, the reflections are measured at neither a reflection mode nor a transmission mode, but are at an angle between 20° and 160° from the emitted light. This mode, termed trans-illumination, shall allow achieving an excellent signal-to-noise ratio that shall enable continuous and reliable measurement of oximetry data on the wrist. In an embodiment the device can include a coherent light scattering (CLS) apparatus adapted to detect the pulse rate. The obtained CLS and PPG data can be correlated so as to minimize or otherwise reject data indicative of motion artifacts.

Correspondingly, US 2011/0082355 A1 discloses a photoplethysmography device and method wherein a PPG measurement is correlated with a dynamic light scattering (DLS) measurement. Light-absorption related blood analyte concentration parameters are measured in accordance with a temporal correlation between the PPG and the DLS measurements.

SUMMARY OF THE INVENTION

It is an object of the present invention to enable blood oxygen saturation measurements with improved reliability. It would be particularly desirable to improve an accuracy of oxygen saturation measurements.

In a first aspect of the present invention a processing device for use in blood oxygen saturation measurement of a subject is presented. The processing device comprises:

an input for receiving first and second detection data of a tissue region of the subject, said first detection data being data acquired over time by detecting radiation at a first wavelength and at a second wavelength received from said tissue region; said second detection data being data acquired over time by detecting radiation at the first wavelength and at the second wavelength received from said tissue region in response to coherent light at the first wavelength and coherent light at the second wavelength being emitted towards the tissue region;

a PPG unit for deriving, from said first detection data, a first PPG signal indicative of an absorption of light within the tissue region at the first wavelength, and a second PPG signal indicative of an absorption of light within the tissue region at the second wavelength;

a flow unit for deriving, from said second detection data, a first flow signal indicative of a flow of light scattering particles within the tissue region probed at the first wavelength, and a second flow signal indicative of a flow of light scattering particles within the tissue region probed at the second wavelength; and a processing unit for correcting said PPG signals based on said flow signals and/or for providing a feedback signal based on a comparison of the first and second flow signals.

In a further aspect of the present invention a system for use in blood oxygen saturation measurement of a subject is presented, the system comprising a coherent light source arranged to emit coherent light at a first wavelength and at a second wavelength towards a tissue region of the subject a detector for acquiring first and second detection data of the tissue region of the subject, said first detection data being acquired over time by detecting radiation at a first wavelength and at a second wavelength received from said tissue region; said second detection data being acquired over time by detecting radiation at the first wavelength and at the second wavelength received from said tissue region in response to the coherent light at the first wavelength and coherent light at the second wavelength being emitted towards the tissue region; and the aforementioned processing device as disclosed herein for processing said first and said second detection data of the tissue region of the subject.

In yet further aspects of the present invention, there are provided a corresponding method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed system, method, computer program and medium can have similar and/or identical preferred embodiments as the claimed device, in particular as defined in the dependent claims and as disclosed herein.

The herein presented solutions provide a possibility to enable blood oxygen saturation measurements with improved reliability. In particular, aspects of the proposed solutions provide a possibility to improve the accuracy of oxygen saturation measurements.

Conventional blood oxygen saturation measurements essentially evaluate a color change of blood due to oxygenated hemoglobin ($HbO_2$) and reduced hemoglobin (Hb). The present invention is based on the idea to further use flow information at the same wavelengths used for blood oxygen saturation measurement as a 'color-blind' method to calibrate or correct the blood oxygen saturation measurement. It has been found that from a flow signal indicative of a flow of light scattering particles within the tissue region, in particular based on interferometric techniques such as laser speckle imaging or laser Doppler, information on the potentially different pulsatile tissue layers probed at the first wavelength and at the second wavelength can be obtained. Hence, the impact of probing a different vasculature at the first wavelength and at the second wavelength can be evaluated. Based on this common concept, according to a first aspect, the PPG signals can be corrected based on said flow signals. According to a second aspect, a feedback signal indicative of a quality or reliability of the PPG signals can be provided.

As used herein, perfusion refers to how much blood flows through a given tissue region, i.e., units of blood volume per time per tissue volume. Perfusion can thus be high even in absence of pulsatile blood volume or pulsatile blood flow, i.e., even be high for a completely non-pulsatile flow. Vice versa, a strong PPG signal can be found in cases of low perfusion, for example, if there is a blockage of flow but high pulsatile input. Hence, as used herein, a (pulsatile) PPG signal originates from the pulsatile blood volume, i.e., is an absorption dominated signal indicative of absorption of light within the tissue region. On the other hand, the (pulsatile) flow signal originates from the (pulsatile) movement of particles within the tissue region. For example, a speckle pattern can be disturbed or a frequency shift can occur due to moving particles. The flow signal can be determined using the principles of Laser Doppler or laser speckle imaging (LSI). PPG signals and flow signals may thus be described as color-based probing of blood absorption and color-blind probing of the blood motion, respectively.

If the same vasculature or pulsatile tissue layers are probed at the first wavelength and at the second wavelength, then the first flow signal should correspond to the second flow signal, because—despite a potentially different absorption—the same blood flow is measured. On the other hand, if different pulsatile tissue layers are probed at the first wavelength and at the second wavelength, there can be a mismatch between the first flow signal and the second flow signal. The mismatch is thus indicative of differences in the probed pulsatile tissue layers, which can then be used (a) to correct the PPG signals and/or (b) to provide a feedback signal.

With (conventional) PPG signals at a first and at a second wavelength alone, it is not possible to distinguish whether the measured absorption at the first and at the second wavelength is caused by (a) the wavelength-dependent absorption properties of oxygenated hemoglobin (HbO2) and reduced hemoglobin (Hb) or (b) probing different pulsatile tissue layers. Probing different pulsatile layers may thus be wrongfully attributed to an incorrect concentration of oxygenated hemoglobin (HbO2) and reduced hemoglobin (Hb). Hence, an over- or underestimated blood oxygen saturation may be provided.

An important aspect is to understand that at least two different wavelengths are used to probe pulsatile vessels. The mechanism in pulse oximetry (POX) is absorption based. SpO2 (arterial oxygen saturation) is estimated from the relative pulsatile PPG signals at these wavelengths because the blood color changes with saturation. Now, if these wavelengths have different penetrations depths and/or probe different pulsatile layers there is a risk that one wavelength probes a layer with highly pulsatile layers more than the other wavelength(s). This can result in a reduced accuracy since some of the difference in PPG amplitude is not due to different absorption but due to different geometrical probing.

Based on this common concept, in a first aspect the PPG signals at the first and the second wavelength can be corrected based on the flow signals at these wavelengths to provide a corrected pulsatile absorption signal. Hence, a difference in the probed pulsatile layers at the first wavelength and at the second wavelength can be corrected for, thereby improving an accuracy of a subsequent determination of a blood oxygen saturation based on the corrected PPG signal.

Based on this common concept, in a second aspect, a feedback signal indicative of a quality of the PPG signals can be provided based on a comparison of the first and second flow signals at the first wavelength and at the second wavelength, respectively. Hence, a mismatch between the probed pulsatile layers at the first wavelength and the second wavelength can be identified. A good correspondence of the two signals can be indicative of a high quality of the PPG signals. However, a mismatch between the PPG signals can be indicative of probing different pulsatile layers. In that case only a reduced reliability of an obtained blood oxygen saturation value can be expected. Such a feedback signal can be particularly advantageous to assess the likelihood of a false alarm. For example, if an alarm signal is determined based on a high quality PPG signal it is very likely a serious event. On the other hand, if an alarm is provided together with feedback about a low quality PPG signal quality, it bears the risk of being a false alarm. For example, a feedback signal indicative of a low PPG signal quality can be issued if a modulation depth (AC/DC) of the first flow signal differs from a modulation of the second flow signal by more than a predetermined threshold.

As used herein, the first wavelength and the second wavelength refer to wavelengths suitable for determining a blood oxygen saturation based thereon, such as for example red and infrared in the wavelength range of 660 nm and 840 or 900 nm. However, also different combinations such as green and red light can be used. More than two wavelengths can be used.

As used herein, first detection data of the tissue region refers to data indicative of detected radiation at a first wavelength ($\lambda 1$) and at a second wavelength ($\lambda 2$) received from said tissue region; and second detection data of the tissue region refers to data indicative of detected radiation at the first wavelength and at the second wavelength received from said tissue region in response to coherent light at the first wavelength and coherent light at the second wavelength being emitted towards the tissue region.

A PPG signal as used herein can be seen as conventional PPG signal indicative of an absorption of light within the tissue region at a given wavelength.

A flow signal as used herein can be obtained by techniques such as laser speckle imaging (LSI) or laser Doppler. Coherent (laser) light scattered from moving objects or particles produces intensity fluctuations that can be used to measure the velocity of the scatterers. An overview of laser Doppler and speckle is given by Briers, "Laser Doppler and time-varying speckle: a reconciliation" in the Journal of the Optical Society of America, vol. 13, no. 2, 1996 as well as in the topical review paper by Briers, "Laser Doppler, speckle and related techniques for blood perfusion mapping and imaging", physiol. Meas. 22, R35-R66, 2001. The flow signal can indicate the degree at which light received from the tissue region of the subject is perturbed by moving particles such as blood cells. In a nutshell, laser Doppler velocimetry uses the frequency shift produced by the Doppler effect to measure velocity. It can be used to monitor blood flow in the body. Laser speckle refers to a random interference effect that gives a grainy appearance to objects illuminated by laser light. If the object comprises individual moving scatterers (such as blood cells), the speckle pattern fluctuates.

As used herein a pulsatile signal indicates a fluctuation due to a cardio-vascular pulse wave travelling through the body of the subject with every heartbeat. On the one hand, the pulse wave will lead to a pulsatile PPG signal indicative of an absorption of light within the tissue region at the first wavelength and at the second wavelength. On the other hand, it will lead to a pulsatile flow signal indicative of a flow or movement of light scattering within the tissue region at the first wavelength and at the second wavelength.

In an embodiment, the system for use in blood oxygen saturation measurement is arranged as a reflectance based system. The solution disclosed herein is particularly advantageous for a reflectance based system because a larger mismatch between light at the first wavelength and at the second wavelength with respect to the probed pulsatile tissue layers can be expected. In a conventional transmission based system, such as a conventional pulse oximetry finger clip, the optical path at the first and the second wavelength can be rather similar.

In a refinement, the proposed system can be arranged as a remote PPG system, in particular comprising a camera as the detector. For the general concept of remote PPG and remote blood oxygen saturation measurement, reference is made to Kong, et al. "Non-contact detection of oxygen saturation based on visible light imaging device using ambient light", Optics Express 21:17464, 2013 and Wieringa, et al., "Contactless multiple wavelength photoplethysmographic imaging: a first step toward "SpO2 camera" technology," Ann. Biomed. Eng. 33, 1034-1041, 2005, which discloses a remote PPG system for contactless imaging of arterial blood oxygen saturation in tissue based upon the measurement of PPG signals at different wavelengths. The system comprises a monochrome CMOS-camera and a light source comprising (incoherent) LEDs of three different wavelengths. A conventional CCD or CMOS camera can be used as the detector unit. Conventional calibration of a remote PPG system based on a calibration curve is described by the inventors in Verkruysse et al., "Calibration of Contactless Pulse Oximetry", Anesthesia & Analgesia, 2016. Camera-based, contactless pulse oximetry is an implementation of RPOX which may particularly benefit from the solution proposed herein. Interrogated skin depths are typically much shallower than in conventional pulse oximeter geometries. It has been found that in a remote PPG system, much of the light contributing to the detected PPG signals only travels through shallow, typically <0.3 mm deep, skin layers.

In an embodiment, the processing unit can be configured to correct said PPG signals based on said flow signals and to provide an output indicative of a blood oxygen saturation of the subject based on said corrected PPG signals. An advantage of this embodiment is that a more accurate blood oxygen saturation value can be determined, since the corrected PPG signals are used for determining an output. Hence, a difference in the probed pulsatile tissue layers can be corrected for. For example, a ratio of ratios of the corrected PPG signals may be provided as the output indicative of the blood oxygen saturation. Based thereon, the blood oxygen saturation may be calculated using a calibration curve or determined using a lookup table in a next step. Alternatively, the processing unit may directly provide the determined oxygen saturation at its output. The oxygen saturation can be determined for example based on the ratio of ratios of the corrected PPG signals in conjunction with a lookup table or calibration curve which provides a correspondence between such a ratio and the corresponding blood oxygen saturation.

In an embodiment, the processing unit can be configured to provide said feedback signal based on said flow signals, said feedback signal being indicative of a quality of the PPG signals and derived from a mismatch between the first flow signal at the first wavelength and the second flow signal at the second wavelength. As explained above, the feedback signal can thus serve as an indicator regarding the reliability of the PPG signal. This can help to distinguish between true and false alarms. Further, if a large mismatch is detected, an operator may reposition the detector and/or light source(s) for acquisition of better signals. The mismatch can be indicative of a different modulation and/or modulation depth (AC/DC) of the flow signals at the first and at the second wavelength.

In an embodiment, the PPG unit can be configured to determine the first and the second PPG signal based on an average of the detected radiation at the first wavelength and at the second wavelength. Spatial and/or temporal averaging can be applied to the detection data at each wavelength. For example, an average light intensity as a spatial average of a region of interest can be determined based of a sequence of image frames of a video signal obtained from a camera as the detection data. In the alternative, for example when processing detection data acquired with a single photodiode, a temporal average can be determined. The averaging time can be selected such that at least two sample values are provided per cardiac cycle. Each PPG signal can indicate a signal trace of the average of the detected data over time. Based thereon, a temporal modulation of this signal trace can be evaluated. Optionally, normalization can be applied.

In an embodiment, the flow unit can be configured to derive the first and/or second flow signal based on laser Doppler and/or laser speckle technique. According to the Doppler principle, light hitting moving particles such as blood cells undergo a change in wavelength/frequency (also referred to as Doppler shift), while light particles which encounter static structures return unchanged. Some of the light can be registered by a detector such as a photodiode. The flow signals can be calculated based on the detection data since the magnitude and frequency distribution of the Doppler shifted light are directly related to the number and velocity of the blood cells. The output signal can thus provide information about the microcirculatory blood flow at the first wavelength and at the second wavelength. For further details, regarding the underlying principles of laser Doppler and laser speckle techniques, reference is made to the aforementioned publications by Briers.

In an embodiment, the flow unit can be configured to determine the first and the second flow signal based on a standard deviation of the detected radiation at the first wavelength and at the second wavelength. A spatial and/or temporal standard deviation of the detection data at each wavelength can be determined. For example, a spatial standard deviation can be determined based on the detected intensities from a spatial region of interest, for example based of a sequence of image frames of a video signal obtained from a camera as the detection data. In the alternative, for example when processing detection data acquired with a single photodiode, a temporal standard deviation of a temporal sequence of measurement values can be determined. Each PPG signal can indicate a signal trace of the standard deviation of the detection data over time. Based thereon, a temporal modulation of the signal traces can be evaluated. Optionally, normalization can be applied.

In contrast to the PPG signals, wherein an average intensity can be evaluated to obtain the PPG signals, the standard deviation can be evaluated to determine the flow signals at the first wavelength and at the second wavelength respectively.

In an embodiment, the flow unit can be configured to determine the first and the second flow signals based on a speckle contrast at the first wavelength and the second wavelength. The speckle contrast can be a temporal or spatial speckle contrast. When a diffuse medium is illuminated with coherent radiation, interference creates a speckle pattern. In absence of motion, the speckle pattern is static. If any of the scatterers moves, the speckle pattern becomes dynamic. Or, with a non-zero acquisition time, the speckle contrast decreases (blurs). Hence the contrast, or standard deviation, goes down which can be interpreted as the flow going up. The flow unit and/or processing unit can thus be configured to evaluate motion blur by detecting speckle contrast variations. For example, a spatial standard deviation over pixels can be divided by an average pixel value. The flow can be inversely proportional to the speckle contrast, 1/SC, where $$SC(t) = \frac{stdev(\text{pixel intensity\_i})}{avg(\text{pixel intensity\_i})}, \qquad (1)$$

with i being the index of the pixels for the image. This approach can use just one single frame to determine a speckle contrast. Alternatively, it is also possible to consider two consecutive frames and find a relative difference between the pixel values. A larger difference in this case indicates a higher flow.

In a refinement, the detector can comprise a plurality of pixels and the signal processor can be configured to determine the pulsatile scattering signal based on a spatial speckle contrast at the first wavelength and at the second wavelength. For example, a spatial speckle contrast can be obtained from an image taken with a camera as the detector units such as a CMOS or CCD camera. An advantage of this embodiment is that a commercially available camera operating at video frame rates can be used such that no high speed detection means are necessary. Laser speckle imaging using a consumer-grade color camera has been demonstrated by Yang et al. in "Laser speckle imaging using a consumer-grade color camera", Optics Letters, Vol. 37, Issue 19, pp. 3957-3959, 2012.

In an embodiment, the processing unit can be configured to correct the first and the second PPG signal based on a temporal modulation of the first and the second flow signal at the first wavelength and the second wavelength. In conventional pulse oximeters the blood oxygen saturation is determined based on the so-called ratio of ratios of the PPG signals, i.e., a ratio of an AC component divided by a DC component of the first PPG signal divided by a ratio of an AC component divided by a DC component of the second PPG signal. This ratio of ratios (RR) can be corrected based on a modulation depth (AC/DC) of the first flow signal at the first wavelength and a modulation depth (AC/DC) of the second flow signal at the second wavelength. Hence, if a light at the first wavelength probes different pulsatile tissue layers than light at the second wavelength, this difference which also has an impact on the absorption of light and thus on the PPG signals at the respective wavelengths, is corrected for and calibrated. In a refinement, the processing unit can be configured to correct the first PPG signal based on the first flow signal at the first wavelength and to correct the second PPG signal based on the second flow signal at the second wavelength.

In an embodiment, the processing unit can be configured to correct the PPG signals by scaling amplitudes of the first and the second PPG signal at the first wavelength and the second wavelength based on amplitudes of the first and the second flow signal at the first wavelength and the second wavelength. Herein, absolute amplitudes or normalized amplitudes can be used.

In a refinement, the processing unit can be configured to determine a ratio of ratios of the PPG signals and to correct said ratio of ratios of the PPG signals based on a ratio of ratios of the flow signals.

In an embodiment, said second detection data can be used as said first detection data. It should be noted that a PPG measurement may use coherent light, whereas a flow measurement, such as laser speckle imaging or laser Doppler as used herein, must use coherent light. Generally speaking, the first and the second detection data can be acquired separately. However, in an embodiment, the second detection data may also be used as the first detection data. An advantage of this embodiment is that the PPG signals and the flow signals can be derived from the same detection data (based on detected radiation acquired in response to coherent light at the first wavelength and at the second wavelength being emitted towards the tissue region).

It shall be understood that known techniques for separating contributions to the detection data at the first wavelength and at the second wavelength such as time division multiplexing, filtering, spectral separation using optical filters arranged in front of respective light sensitive areas of the detector, and the like can be applied.

A signal processor or processor configured to perform the steps of the processing method described herein can, for example, refer to a microcontroller, digital signal processor (DSP), FPGA, general purpose CPU, or the like. It should further be noted, that the processing device and/or processor described herein can also be implemented as a distributed processing device or a cloud base service, where different processing steps may be executed by different physical entities at the same or different geographic locations.

BRIEF DESCRIPTION OF THE DRAWINGS

These and other aspects of the invention will be apparent from and elucidated with reference to the embodiment(s) described hereinafter. In the following drawings FIG. 3 shows a schematic diagram of a second embodiment of a system according to an aspect of the present invention, FIG. 4 shows a schematic diagram of a third embodiment of a system according an aspect of to the present invention, FIG. 5A a shows a diagram of blood absorption coefficients of oxygenated hemoglobin ($HbO_2$) and reduced hemoglobin (Hb) versus wavelength, FIG. 5B shows diagrams of pulsatile intensity modulation at a first and at a second wavelength versus time, FIG. 6A shows a transmission-based measurement through a tissue region, FIG. 6B shows a diagram of a relative intensity contribution to detected intensity versus skin depth for the transmission-based measurement as shown in FIG. 6A, FIG. 6C shows an exemplary pulsatility profile versus skin depth;

FIG. 7A shows a schematic diagram of a reflectance-based measurement of a tissue region;

FIG. 7B shows a diagram of a relative intensity contribution to detected intensity versus skin depth for the reflectance-based measurement as shown in FIG. 7A, FIG. 7C shows a diagram of a pulsatility profile versus skin depth, FIG. 8A shows a diagram of camera-based blood oxygen saturation versus reference blood oxygen saturation, FIG. 8B shows a diagram of blood oxygen saturation with a finger probe versus reference blood oxygen saturation, FIG. 9 shows a diagram of deviations of repeated blood oxygen saturation measurements for a plurality of subjects at different days, FIG. 15A shows two examples of light at a first wavelength and at a second wavelength having unequal penetration depths and different vascular pulsatility profiles, as indicated by the insets on the right of the graphs in FIG. 15A, respectively, FIG. 15B shows diagrams of exemplary PPG signals at the first and at the second wavelength for the first vascular pulsatility as indicated in FIG. 15A (upper graphs) and the second vascular pulsatility profile as indicated in FIG. 15A (lower graphs), FIG. 15C shows diagrams of the corresponding flow signals at the first and at the second wavelength for the first vascular pulsatility profile as indicated in FIG. 15A (upper graphs) and the second vascular pulsatility profile as indicated in FIG. 15A (lower graphs)

DETAILED DESCRIPTION OF EMBODIMENTS

Figure 1:
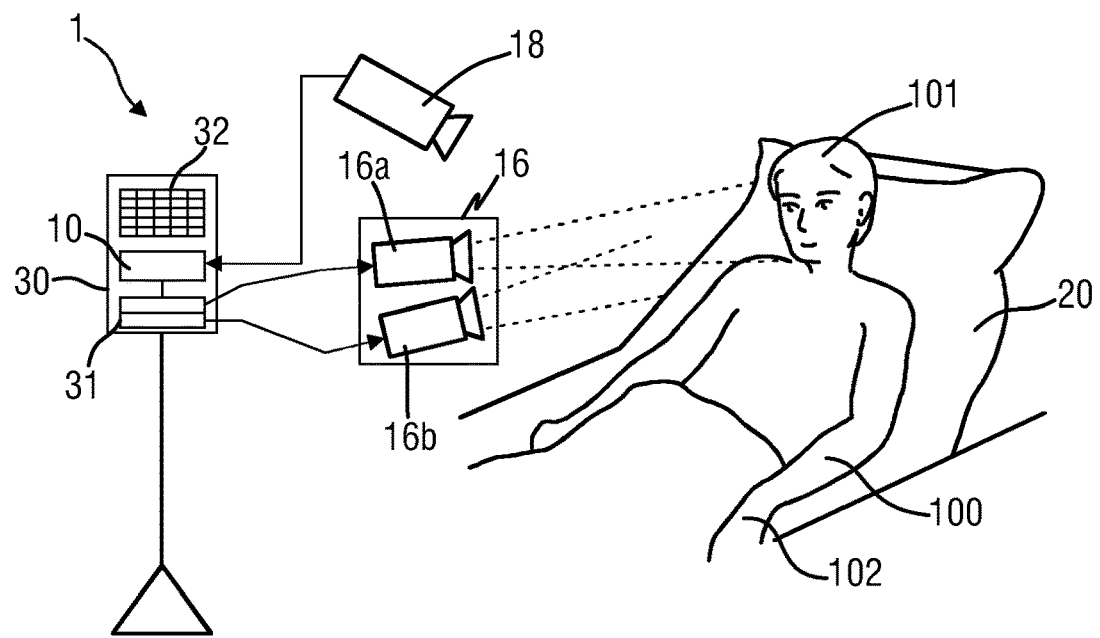
FIG. 1 shows a schematic diagram of a first embodiment of the system according to an aspect of the present invention.

FIG. 1 shows a schematic diagram of a first embodiment of a system 1 and a processing device 10 for use in blood oxygen saturation measurement of a subject 100 according to an aspect of the present invention. Hereinafter, the processing device 10 may be briefly referred to as device 10. The subject 100, in this example a patient lies in a bed 20, e.g., in a hospital or other healthcare facility, but may also be a neonate or premature infant, e.g. lying in an incubator, or a person at home or in a different environment such as a sports or leisure activity setting.

Besides the device 10, the system 1 comprises a coherent light source 16, also referred to as illumination source or illumination unit, arranged to emit coherent light at a first wavelength λ1 and at a second wavelength λ2 towards a tissue region of the subject 100. In the shown embodiment, the coherent light source 16 comprises a first laser source 16A, in particular comprising a laser diode for emitting coherent light at the first wavelength, and a second laser source 16B, advantageously also comprising a laser diode for emitting coherent light at the second wavelength. The coherent light source 16 thus is arranged to emit coherent light at a first wavelength λ1 and at a second wavelength λ2 towards a tissue region 101 of the subject 100, for example to the forehead of the subject or other bare skin region such as a hand or arm region 102.

The system 1 further comprises a detector 18 for acquiring first and second detection data of the tissue region of the subject said first detection data being acquired over time by detecting radiation at a first wavelength and at a second wavelength received from said tissue region, said second detection data being acquired of a time by detecting radiation at the first wavelength and at the second wavelength received from said tissue region in response to coherent light at the first wavelength and coherent light at the second wavelength being emitted towards the tissue region by the coherent light source 16. Based on the first and second detection data, the device 10 can derive PPG signals and flow signals as will be explained in more detail further below.

There exist different embodiments for a detector (also referred to as acquisition device or a signal acquisition unit), for detecting electromagnetic radiation in form of light at the first and at the second wavelength. In the embodiment shown in FIG. 1, the detector 18 can be a camera such as a CCD or CMOS camera. For the general concept of remote PPG and remote blood oxygen saturation using a camera, reference is made to the aforementioned paper by Verkruysse et al. the content of which is incorporated herein by reference.

For acquiring detection data of the tissue region 101 of the subject 100, the detector 18 comprises a camera including a suitable photo sensor for (remotely and unobtrusively) capturing image frames of the subject 100 in particular for acquiring a sequence of image frames of the subject 100 as detection data over time. The image frames captured by the camera may in particular correspond to a video sequence captured by means of an analog or digital photo sensor, e.g. in a (digital) camera. Such a camera can comprise a CMOS or CCD sensor, which may also operate in a specific spectral range (visible, IR) or provide information for different spectral ranges such as R, G, B channels. The image frames can include a plurality of image pixels having associated pixel values. In particular, the image frames can include pixels representing light intensity values captured with different photosensitive elements of a photo sensor. These photosensitive elements may be sensitive in a specific spectral range (i.e., representing a specific color or wavelength). The image frames include at least two groups of some image pixels each being representative of a different skin region of the subject, e.g., the forehead, the cheek, the throat, the hand, etc. Thereby, an image pixel may correspond to one photosensitive element of a photo-detector and its (analog or digital) output may be determined based on a combination (through binning) of a plurality of the photosensitive elements.

Different approaches exist for separating contributions of light detected at the first wavelength and at the second wavelength. For example, the detector 18 can comprise filters adapted for transmission at the first and filters adapted for transmission at the second wavelength to distinguish between the contributions at the first wavelength and at the second wavelength in the spectral domain. In the alternative or in addition, time division multiplexing can be applied. For example, a light control unit 31 can be provided which controls the emission of light at the respective first and second wavelength by the coherent light source 16. The contributions at different wavelengths can thus be separated in time domain from the output signal of the detection unit 18 comprising the detection data.

The device 10 is further preferably connected to an interface for displaying the determined signals and/or information and/or for providing medical personnel with an interface to change settings of the device 10, the coherent light source 16, the detector 18 and/or any other parameters of the system 1. Such an interface 32 may comprise different displays, buttons, touchscreens, keyboards, communication interfaces or other human machine interface (HMI) means. A common control unit 30 can comprise the device 10, the light control unit 31 and optionally also the interface 32. The control unit 30 can be a patient monitor comprising additional functionalities.

Optionally, the interface 32 can be configured to provide information indicative of a quality of the PPG signals to a user, for example, in case the processing unit is configured to provide a feedback signal based on a comparison of the first and second flow signals. The feedback signal can be indicative of a mismatch between the first flow signal and the second flow signal. The feedback signal can thus assist a user in determining whether and/or when a reliable pulse oxygen saturation can be measured.

A system 1 as illustrated in FIG. 1 may, e.g., be located in a hospital, healthcare facility, elderly care facility, neonate intensive care unit (NICU) or the like. Apart from the monitoring of patients, aspects of the present invention may also be applied in other fields such as neonate monitoring, general surveillance applications, security monitoring or so-called lifestyle environments such as fitness equipment, wearable devices, or handheld-devices like a smartphone or the like. The uni- or bidirectional communication between the device 10, the detector 18, the coherent light source 16 and the interface 32 may work via a wireless or wired communication interface. Other embodiments of the present invention may include a device 10, which is not provided stand-alone but integrated into another system component such as the detector 18, the interface 32 or a patient monitor. Furthermore, the device 10 can be implemented as a distributed device by a plurality of components, including a cloud-based solution wherein at least some of the processing steps are performed at a remote location.

Figure 2:
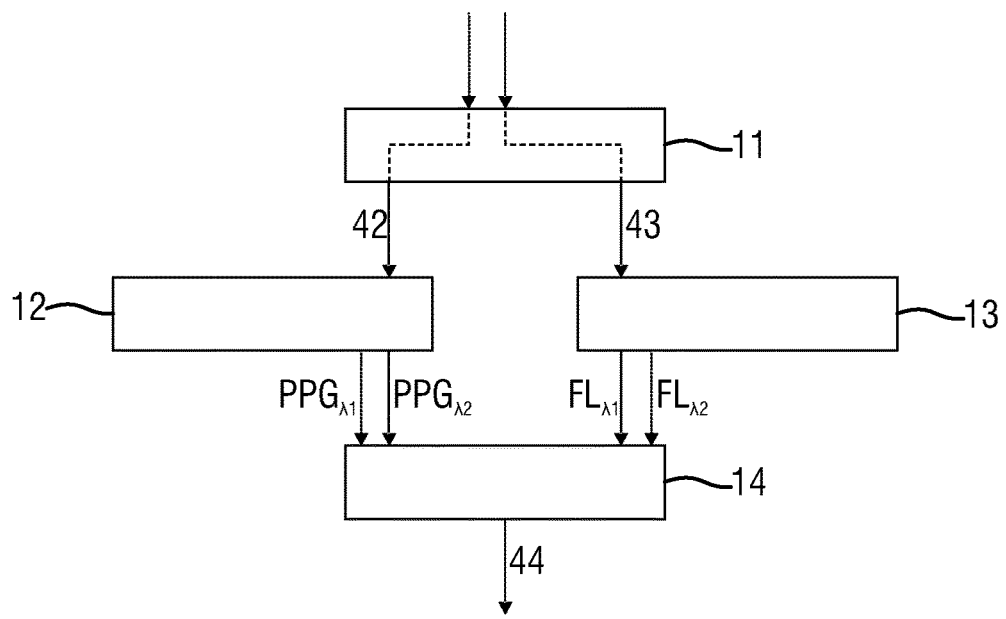
FIG. 2 shows a schematic diagram of a first embodiment of a processing device according to an aspect of the present invention.

FIG. 2 shows a schematic diagram of a first embodiment of a device 10 according to an aspect of the present invention, which may be used as device 10 in the system 1 shown in FIG. 1. The device 10 comprises an input or input interface 11 for obtaining, i.e. receiving or retrieving, first and second detection 42, 43 data of the tissue region of the subject, said first detection data 42 being data acquired over time by detecting ration at a first wavelength and at a second wavelength received from said tissue region; said second detection data 43 being data acquired over time by detecting radiation at the first wavelength and at the second wavelength received from said tissue region in response to coherent light the first wavelength and coherent light at the second wavelength being emitted towards the tissue region.

The device 10 further comprises a PPG unit 12 for deriving, from said first detection data 42, a first PPG signal $PPG_{\lambda 1}$ indicative of an absorption of light within the tissue region at the first wavelength and a second PPG signal $PPG_{\lambda 2}$ indicative of an absorption of light within a tissue region at the second wavelength. The device 10 further comprises a flow unit 13 for deriving, from said second detection data 43, a first flow signal $FL_{\lambda 1}$ indicative of a flow of light scattering particles within the tissue region of the subject probed at the first wavelength, and a second flow signal $FL_{\lambda 2}$ of a flow of light scattering particles within the tissue region of the subject probed at the second wavelength. A processing unit 14 is provided for correcting said PPG signals $PPG_{\lambda 1}$, $PPG_{\lambda 2}$ based on said flow signals $FL_{\lambda 1}$, $FL_{\lambda 2}$ and/or for providing a feedback signal based on a comparison of the first and the second flow signals $FL_{\lambda 1}$, $FL_{\lambda 2}$ which can be provided as an output 44 of the device 10.

The PPG unit 12, the flow unit 13 and the processing unit 14 can be implemented in hard- and/or software, for example, by one or more programmed processors or computers.

FIG. 1 shows an embodiment, wherein the system 1 is arranged for non-contact, i.e., remote measurement. FIG. 3 and FIG. 4 show a second and a third embodiment of a system 1 for use in blood oxygen saturation measurement of a subject arranged for contact-based measurement.

In the embodiment shown in FIG. 3, the system 1 for use in blood oxygen saturation measurements of the subject comprises a finger clip 34 and a control unit 30. The control unit 30 in turn comprises the device 10 and a light control unit 31 for operating a coherent light source 16. A finger clip for use in pulse oximetry can take various forms as known in the art. A conventional finger clip for pulse oximetry typically comprises a red LED as the first light emitter for emitting light at a first, red wavelength, for example at 660 nm, and a second, infrared LED, for example at 840 or 900 nm, for emitting infrared light towards a tissue region of the subject, here as a transmission-based measurement through the finger 103 of the subject. The finger 103 comprises blood vessels 104 which are probed thereby.

In the embodiment shown in FIG. 3, a coherent light source 16 is provided comprising a first laser source 16a in form of a red laser diode 16A for emitting coherent light at a first, red wavelength towards the finger 103 comprising the blood vessels 104 to be probed, and a second lasers source 16b in form of an infrared laser diode, for emitting coherent radiation at a second, infrared wavelength towards the same tissue region of the subject.

The detector 18 in the shown embodiment comprises a first photodiode 18a and a second photodiode 18b. A narrow band red filter centered at the first wavelength of the first laser source 16a can be provided in front of the first photodiode 18a and a second filter centered at the second wavelength of the second laser source 16b can be provided in front of the second photodiode 18b. Thereby, contributions at the first wavelength and at the second wavelength can be distinguished in the spectra domain. In the alternative, as shown in FIG. 4, a single detector element such as a single photo diode can be provided and the signals may be separated for example by time division multiplexing and controlling the light control unit 31 for the first laser source 16a and a second laser source 16b accordingly. The detection data from the detector 18 is provided to the device 10, where it can be processed as described with reference to FIG. 2

FIG. 4 shows a third embodiment of a contact-based system 1 for use in blood oxygen saturation measurement according to an aspect of the present invention. As shown in FIG. 4, the probe is applied to a finger 103 of a subject comprising blood vessels 104 to be probed. In the shown embodiment a single photodiode is provided as a detector 18 which provides detection data of the tissue region of the subject to the device 10. In the shown embodiment, the coherent light source 16 comprising the first laser source 16a and the second laser source 16b can be integrated into the probe 35. The probe 35 is arranged for attachment to the skin of the subject.

It should be noted that a probe as shown in FIG. 4, also referred to as a surface measurement probe, can also be applied to other body parts such as the forehead of the subject and a transmission-based solution as shown in FIG. 3 can also be applied in different forms, for example arranged for being wrapped around a foot of a newborn in a neonatology department.

It shall be understood that it is not mandatory to use coherent light for obtaining the first detection data from which the PPG signal can be derived. Hence, in the embodiments shown in FIGS. 1, 3 and 4, a non-coherent light source can be provided or even ambient light can be used for obtaining the first detection data at the first wavelength and at the second wavelength. However, advantageously the second detection data, i.e., data being acquired over time by detecting radiation at a first wavelength and at a second wavelength received from said tissue region in response to coherent light at the first wavelength and coherent light at the second wavelength being emitted towards the tissue region, is also used as the first detection data.

In the following, more details of aspects of the present invention, further embodiments and the underlying principles will be explained.

Pulse oximetry generally measures blood oxygen saturation, also referred to SpO2, by comparing relative PPG amplitudes at different wavelengths (amplitudes defined as AC/DC), for example at a first wavelength and at a second wavelength such as red and infrared, because these relative amplitudes depend strongly on the blood oxygenation. For pulse oximetry to work properly, two conditions are to be met: (1) only arterial blood vessels are pulsatile and (2) the wavelengths at which PPG signals are measured to probe the same vasculature or pulsatile tissue layers. If one or both of these assumptions are not valid, serious inaccuracies in SpO2 estimates may result. The solution proposed herein addresses a validation of the second assumption and/or a correction for errors introduced when the assumption is invalid.

FIG. 5A shows the blood absorption coefficients $\mu_a$ for oxygenated hemoglobin HbO2 and reduced hemoglobin Hb. As shown in FIG. 5A, the blood absorption coefficients are strongly wavelength dependent. By measuring an absorption of light within a tissue region of interest at the first wavelength λ1, for example red, and measuring an absorption of light within the tissue region at a second wavelength λ2, for example infrared, a ratio of the concentrations of oxygenated hemoglobin HbO2 and reduced hemoglobin Hb can be derived.

FIG. 5B shows diagrams of a first PPG signal $PPG_{\lambda,1}$ and a second PPG signal $PPG_{\lambda,2}$. The signals can also be referred to as pulsatile PPG signals. In the diagrams, the vertical axis denotes the detected radiation, i.e. the received light intensity I, whereas the horizontal axis denotes the time t.

For determining the blood oxygen saturation by photoplethysmography at least two wavelengths are required, as exemplary explained below. Contact pulse oximeters typically transmit red (R) and infrared (IR) (or, more precisely, in some cases near infrared) light through a vascular tissue of the subject of interest. The respective light portions (R/IR) can be transmitted and detected in an alternating (fast-switching) manner. Given that the respective spectral portions are differently absorbed by oxygenated hemoglobin (HbO$_2$) and reduced hemoglobin (Hb), blood oxygen saturation eventually can be processed. An oxygen saturation (SO$_2$) estimation algorithm can make use of a ratio of the signals related to the red and the infrared portion. Furthermore, the algorithm can consider a non-pulsatile signal component. Typically, the PPG signal comprises a DC component and a relatively small pulsatile AC component. Furthermore, SO2 estimation generally involves an empirically derived calibration factor applied to the processed values. Typically, the calibration factor (or, calibration curve) is determined upon reference measurements involving invasive blood oxygen saturation measurements. A calibration factor is required since a PPG device basically detects a ratio of (spectral) signal portions which has to be transferred into a blood oxygen saturation value which typically involves a ratio of HbO$_2$ and Hb. For instance, but not intended to limit the present disclosure, blood oxygen saturation estimation can be based on the following general equation:

$$SO_2 = \frac{HbO_2}{HbO_2 + Hb}, \qquad (2)$$

whereas PPG devices merely mediately detect HbO$_2$ and Hb from the spectral response at at least two wavelengths.

Generally, a measured PPG signal $PPG_{\lambda,1}$, $PPG_{\lambda,2}$ as a characteristic signal is considered to contain a considerably constant (DC) portion and an alternating (AC) portion superimposing the DC portion. Applying signal processing measures, the AC portion can be extracted and, furthermore, compensated for disturbances. For instance, the AC portion of the characteristic signal can comprise a dominant frequency which can be highly indicative of the subject's 100 vascular activity, in particular the heartbeat. Still, the characteristic signal, in particular the AC portion, can be indicative of further vital parameters. In this connection, the detection of arterial blood oxygen saturation is an important field of application. Basically, arterial blood oxygen saturation-representative values can be computed taking into account the behavior of the AC portion of the PPG signals at distinct spectral portions. In other words, a degree of arterial blood oxygen saturation can be reflected in different radiation absorbance at blood vessels. Furthermore, one can make use of the fact that the difference in absorbance due to the grade of oxygenation also varies significantly across different spectral portions. Moreover, also the DC portion of the signal can be utilized for blood oxygen saturation detection. Typically, the DC component represents the overall light absorption of the tissue, venous blood, and non-pulsatile arterial blood. By contrast, the AC component may represent the pulsatile arterial blood's absorption. Consequently, the determination of arterial blood oxygen saturation (SaO$_2$) can be expressed as:

$$SaO_2 = C \cdot \frac{(AC/DC)_{red}}{(AC/DC)_{infrared}}, \qquad (3)$$

where C is a calibration parameter. C may stand for a large variety of calibration parameters applicable to the AC/DC relationship and should therefore not be interpreted in the strict algebraic sense of equation (2). C may, for example, represent a fixed constant value, a set of fixed constants or an adjustable calibration parameter. By way of example, another exemplary SaO2 derivation model can be expressed as:

$$SaO_2 = C_1 + C_2 \cdot \frac{(AC/DC)_{red}}{(AC/DC)_{infrared}}, \qquad (4)$$

where $C_1$ and $C_2$ can be considered calibration parameters of a linear approximation. In an exemplary embodiment, the signal calibration parameter determination can be directed to adjust or adapt the parameter $C_1$. Still, in the alternative, SaO$_2$ derivation may also be based on value tables deposited in (or accessible by) the system 1 and/or device 10. The value tables (lookup-tables or data bases) may provide for a discrete representation of the relationship between detected PPG signals und the desired calibration parameter. Also in that case an adaptable calibration parameter may be applied to improve the accuracy of the vital parameter determination.

It should be understood that the equations (2) and (3) are primarily presented for illustrative purposes. They should not be construed as limiting the scope of the present disclosure. In practice, the skilled person may determine and establish further appropriate $SaO_2$ derivation models. Alternative wavelength combinations, for example green and red, can be used depending on the substance to be detected.

FIG. 6A and FIG. 7A illustrate differences in light paths in two pulse oximetry light-detection geometries. FIG. 6A illustrates a light interrogation path for transmission-based pulse oximeter probe such as a finger-clip pulse oximeter configuration. FIG. 7A illustrates a light interrogation path in a remote setup such as a camera-based setup. In FIG. 6A and FIG. 7A, the light source is denoted by Tx and the receiver or detector is denoted by Rx.

Conventional transmission-based probes, as shown in FIG. 6A can probe relatively deep vascular layers, typically >1 mm, while in contactless, in particular camera-based PPG, the interrogation depth is much shallower, typically <0.3 mm. This means that different skin layers are probed and possibly, different vascular layers, which may have different levels of volumetric pulsatility and micro vascular shunting pathways. Pulsatility dissipates as the cardiovascular pulse travels from the arteries to arterioles. It is typically assumed that volume pulsatility does not exist in capillaries any more. In the skin, arterioles rise from the deeper layer towards the surface where they branch in two capillaries. Hence, probing different depths potentially means probing a different vasculature.

It has been found that differences in light paths, in particular differences in light paths at the first wavelength and at the second wavelength, can have negative impact on the accuracy for several reasons such as:

(1) If capillaries in the papillary dermis are even slightly pulsatile and have slightly lower oxygen saturation than arterial blood, the much higher sampling weight caused by detected intensity I (z) at a skin penetration depth z, may still have large impact on the SpO2 estimate. In other words, the first assumption would not be valid and is exposed by the different interrogation depths.

(2) If hardly any pulsatility exists in the papillary dermis, not only the relatively thin epidermis is a source of shunt light, but the papillary dermis layer as well. It then contributes to the DC part in the PPG signal without contributing to the AC. Differences in penetration depths, leading to differently affected DC levels, can cause that a AC/DC estimate, i.e., the PPG amplitude or modulation depth, is not just an illumination intensity normalized PPG signal any more, and thus the ratio of the two PPG amplitudes does not provide an accurate estimate of SpO2 anymore.

(3) Related to (2), if one wavelength penetrates deeper through a low-pulsatile layer, while the other wavelength hardly sees through this layer, the two wavelengths may have different PPG amplitudes.

As can be seen from a comparison of FIG. 6A and FIG. 6B compared to FIG. 7A and FIG. 7B, a transmission-based pulse oximeter having a light source-detector (Tx-Rx) geometry as shown in FIG. 6A, has a much deeper interrogation depth as shown in the relative contribution to detected intensity I(z) shown in FIG. 6B. On the other hand, a remote or camera-based pulse oximeter having a source-detector (Tx-Rx) geometry as shown in FIG. 7A has a much shallower interrogation depth as indicated by the exponential decay shaped curve of the relative contribution to the detected intensity I(z) shown in FIG. 7B. It should further be noted that the actual pulsatility profile of the probed tissue volume is typically not known. FIG. 6C and FIG. 7C show an assumed pulsatility P(z) versus skin penetration depth z.

In particular for the reflectance based case shown in FIG. 7A, radiation emitted towards the tissue region may have different penetration depths at the first wavelength and as at the second wavelength, for example, at a red and an infrared wavelength. It should further be understood that the penetration depth can also vary in time when optical and/or physiological properties of the tissue vary, for example due to venous pooling or vasoconstriction or -dilation. If pulsatility varies between vascular layers, the difference in penetration depth can disturb the SpO2 calibration and consequently the accuracy.

In view of the above, the proposed solution can be particularly advantageous for remote SpO2 measurement using a camera, because due to its illumination-detection geometry, it may suffer from the invalid assumption that red and infrared wavelength, or any other combination of wavelengths used for deriving SpO2, would interrogate the same skin depths.

Referring now to FIGS. 8A and 8B, the different penetration depth of the different wavelengths in the interrogated tissue might be a cause for the relatively larger spread in the camera-based method for SpO2 measurement shown in the diagram in FIG. 8A, as compared to the spread in the transmission-based finger probe measurement shown in FIG. 8B. The vertical axis denotes the SpO2 measured with a PPG camera in FIG. 8A and a finger probe in FIG. 8B. The horizontal axis denotes a reference SpO2 measurement.

In FIG. 8A and FIG. 8B, each dot indicates a median value over an entire SpO2(t) trace of several minutes. Each point thus represents one individual subject, at a certain oxygenation level. Therefore, any deviation from the x=y axis represents an SpO2 offset or 'calibration', error. Nonetheless it can be seen that in terms of FDA approval the SpO2 camera is also close to a finger pulse oximeter. The upper and lower parallel line to the y=x axis denote a <3% RMS (root mean square) error margin for FDA approval.

It should further be noted that a remote measurement by for example an SpO2 camera, may suffer more from the effects of shunt light if the different wavelengths probe different tissue depths. The DC levels and thus the AC/DC ratios may be differently affected by the optical shunting independently of the SpO2, which may lead to miscalibration and inaccuracy.

In this context, FIG. 9 shows a graph of repeated blood oxygen saturation measurements for a number of volunteers repeated on different days which show a reproducibility of relative SpO2 deviation with respect to a group calibration. The vertical axis in FIG. 9 denotes a deviation A between a measured and a reference SpO2 value, $\Delta SpO2(\%)$. The horizontal axis gives the different volunteers V labeled from 1 to H. The number of repeated measurements n is given below. As can be seen from FIG. 9, some individuals repeatedly show an overestimation while others repeatedly show an underestimation. Such an individual bias suggests that pulsatile layers may indeed be interrogated to a larger extent by one wavelength than by the other. The results shown in FIG. 9 are given for camera-based pulse oximetry. It should be noted that specular reflected light from the tissue surface contributes to DC only, not to AC. Specularly reflected light is thus pure shunt light, i.e. light that did not travel into the skin before it was emitted towards the detector to be detected, which can distort the ratio of ratios on which the determination of the blood oxygen saturation is based.

While conventional pulse oximetry devices only evaluate a PPG signal at a first wavelength and as a second wavelength for example in a transmission-based setup using a finger clip or a red LED and an infrared LED transmit light towards for example a finger of the subject, the solution according to an aspect of the present invention suggests to perform a blood oxygen saturation measurement using coherent—rather than conventionally used incoherent—light sources such as cheap diffuse laser diodes, at a wavelength appropriate for SpO2 monitoring and/or imaging, to allow (near-) a simultaneous acquisition of PPG signals and flow signals indicative of a flow of lights scattering particles within the tissue region of the subject. Such a flow signal can be obtained using, for example, laser Doppler and/or laser speckle techniques such as laser speckle imaging. Hence, the flow signals, for example laser speckle images, and the modulations therein can be used to correct the PPG signals at the first and at the second wavelength for different potential penetration depths at the different wavelength and the associated miscalibrations to allow for assessment with improved accuracy.

Figure 10A:
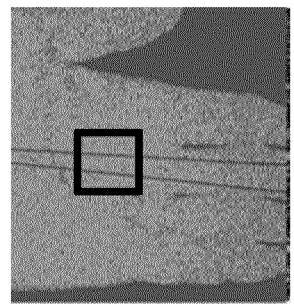
FIG. 10A shows an image of detected radiation using a camera as the detector.

FIG. 10A shows an illustration of data acquisition with a camera-based setup. A 'raw', laser speckle image can be created using the same first and second for example red and infrared, wavelength, as used in a conventional PPG measurement. A tissue region that is used for the measurement is indicated by the rectangle in FIG. 10A. A corresponding image is obtained at the first wavelength and at the second wavelength. It should be noted that further wavelengths can be used. Based on a series of such images, for example, images of a video signal acquired by a CCD or CMOS camera, detection data can be acquired over time.

Figures 10B, 10C:
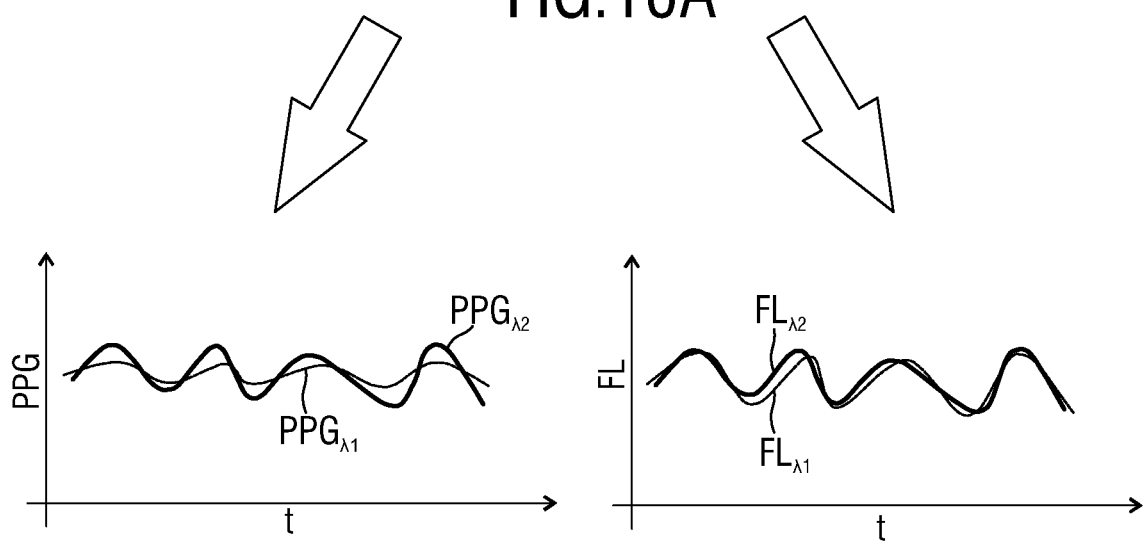
FIG. 10B shows a diagram of PPG signals at a first and at a second wavelength versus time.
FIG. 10C shows a diagram of flow signals at a first and at a second wavelength versus time, corresponding to the PPG signals shown in FIG. 10B.

FIG. 10B shows exemplary PPG signals at the first wavelength and at the second wavelength, wherein each PPG signal is indicative of an absorption of light within the tissue region at the respective wavelength. At each wavelength the PPG signal can be calculated by $$PPG_\lambda(t) = \frac{<I_\lambda>(t)}{<I_\lambda>_{DC}}, \quad (5)$$

where $<I>$ is an average pixel or intensity value over a region of interest (ROI) of an image frame as indicated by the rectangle in FIG. 10A, and $<I>_{DC}$ is an average pixel or intensity value over the region of interest averaged over time, in particular averaged over several cardiac periods. The absorption-based PPG signal can be seen as a 'color-based', probing of pulsatility. The PPG signal $PPG_{\lambda 1}$, here obtained using red light, has a smaller PPG amplitude indicating a smaller absorption coefficient for HbO2 at $\lambda 1$ compared to a higher absorption at a second wavelength, here using infrared light.

The approach disclosed herein further suggests combining such a conventional PPG measurement with a flow measurement to obtain a first and a second flow signal indicative of a flow of light scattering particles within the tissue region of the subject at the first wavelength and at the second wavelength. Such a measurement can be performed as a 'color blind', measurement based on interferometric techniques such as laser speckle imaging or Doppler. In the example shown in FIG. 10C laser speckle imaging is used to determine the flow.

FIG. 10C shows a first flow signal $FL_{\lambda 1}$ indicative of a flow of lights scattering particles within the tissue region of the subject at the first wavelength $\lambda 1$, and a second flow signal $FL_{\lambda 1}$ indicative of a flow of lights scattering particles within the tissue region of the subject at the second wavelength $\lambda 2$.

In the example shown in FIG. 10C, the slow signal at a first and second wavelength $FL_{\lambda 1}$ and $FL_{\lambda 2}$ can be calculated by determining a speckle contrast as a laser speckle imaging signal by $$FL_\lambda(t) = LSI_\lambda(t) = \frac{\sigma_\lambda(t)}{<I_\lambda>(t)}, \quad (6)$$

where $\sigma$ is the standard deviation over pixels in the region of interest and $<I>$ is an average pixel or intensity value over the region of interest of an image frame. The flow signal is pulsatile due to pulsatile flow. For equal penetration depths, a modulation of the flow signal (ratio of AC/DC) would be the same both wavelengths.

The proposed solution is thus based on a combination of a conventional 'color-based' PPG measurement and a 'color blind' flow measurement based on interference effects. It should again be highlighted that an interferometric or a speckle-based technique such as LSI requires coherent (laser) light because it is an interferometric technique. The speckle pattern can be seen as an interferogram which blurs upon motion. The absorption-based PPG signal may use coherent light but can also work with incoherent light sources.

In an embodiment, the proposed device 10 and/or system 1 can be implemented by two or more separate physical entities. These entities can be wired or wirelessly connected and exchange data and/or information, for example using a data numeric interface, or Bluetooth, Wi-Fi and the like.

For example, the proposed device 10 and/or system 1 can be implemented by a flow measurement device and a pulse oximeter device. They can be provided as separate physical entities. The pulse oximeter device can comprise a first input for receiving the first detection data, said first detection data being data acquired over time by detecting radiation at a first wavelength ($\lambda 1$) and at a second wavelength ($\lambda 2$) received from said tissue region. The flow measurement device can comprise a second input for receiving the second detection data, said second detection data being data acquired over time by detecting radiation at the first wavelength and at the second wavelength received from said tissue region in response to coherent light at the first wavelength and coherent light at the second wavelength being emitted towards the tissue region. Referring to FIG. 2, the input 11 can thus be implemented comprising said first input and said second input.

In this embodiment, the pulse oximeter device can comprise the PPG unit 12 for deriving, from said first detection data, a first PPG signal indicative of an absorption of light within the tissue region at the first wavelength, and a second PPG signal indicative of an absorption of light within the tissue region at the second wavelength. Correspondingly, the flow measurement device can comprise the flow unit 13 for deriving, from said second detection data, a first flow signal indicative of a flow of light scattering particles within the tissue region at the first wavelength, and a second flow signal indicative of a flow of light scattering particles within the tissue region at the second wavelength.

Optionally, the flow measurement device may comprise a first coherent light source arranged to emit coherent light at a first wavelength and at a second wavelength towards a tissue region of the subject. Optionally, the flow measurement device may comprise a detector for acquiring the second detection data. Optionally, the pulse oximeter device may comprise a second light source arranged to emit coherent or non-coherent light at the first wavelength and at the second wavelength towards a tissue region of the subject. Optionally, the pulse oximeter device may comprise a second detector for acquiring the first detection data. It shall be understood that advantageously a detector and/or a coherent light source can be shared by the flow measurement device and the pulse oximeter device.

In this embodiment, the processing unit 14 for correcting said PPG signals based on said flow signals and/or for providing a feedback signal based on a comparison of the first and second flow signals can at least in part be comprised in the flow measurement device, the pulse oximeter device and/or a further physical entity. The processing unit can also be distributed between, for example, the pulse oximeter device and the flow measurement device. For example, a ratio of ratios can be determined based on the flow signals in the flow measurement device as correction data for correcting said PPG signals based thereon. The pulse oximeter device can comprise an input for receiving said correction data and can further be configured to correct the PPG signals based thereon.

It shall be understood that the pulse oximeter device may not constantly have to be provided with correction data. It can be sufficient to provide such correction data for correcting said PPG signals based on said flow signals, for example, only at the beginning of a measurement, in time intervals or when it has been determined that the measurement conditions have changed. In such a case, it can be sufficient to perform the flow measurement only when needed for calibration, whereas the PPG measurement may be performed over an extended period of time. For example, the pulse oximeter device can constantly monitor the subject, while the flow measurement device for measuring the flow signals at the first and at the second wavelength is only provided for calibration. Advantageously, such a flow measurement device may even be shared between multiple subjects.

The examples shown in FIG. 10A to FIG. 10C represent the case in which red and infrared light probe the same vasculature. LSI modulation depths are substantially the same while PPG modulation depths reflect the different absorption coefficient for the arterial blood. The flow signal modulation depths (AC/DC) from the two wavelengths should be similar if similar tissue layers are probed, because the scattering of speckle dynamics are not or at least not to the same extent affected by absorption.

However, if the flow signal modulation depths at the two wavelengths differ, this can indicate that the penetration depth was different and that one wavelength 'sees' a layer with more pulsatile vasculature than the other. In consequence, a ratio between modulation depths of the first and second flow signal at the first and at the second wavelength can be used to correct the ratio of ratios (RR) of the PPG signals at the first and at the second wavelength. In this way, the SpO2 measurement can be corrected for differences in penetration depth of the two wavelengths.

Figure 11:
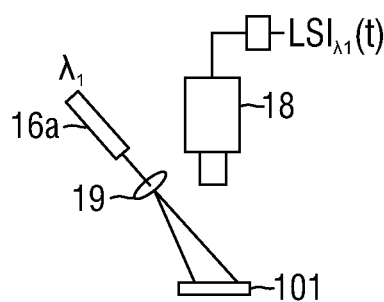
FIG. 11 shows a schematic diagram of a laser speckle imaging set up.
Figure 12:
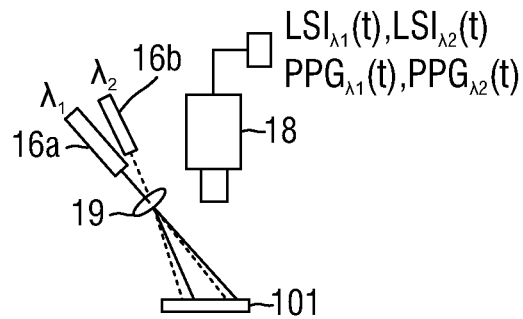
FIG. 12 shows a modification of the laser speckle imaging set up of FIG. 11 adapted as a system according to an aspect of the present invention.

FIG. 11 and FIG. 12 illustrate the differences between a conventional laser speckle imaging setup and an embodiment of the system for use in blood oxygen saturation as disclosed herein. The laser speckle imaging setup shown in FIG. 11 comprises a single laser source 16a for emitting coherent light at only one wavelength λ1 towards a tissue region 101 of a subject. An optional expander 19 can be provided for expanding the beam of the coherent light source 16a. The illuminated tissue region 101 is imaged by a camera, here a CCD camera, as a detector 18. Based on the output signal of the camera, a laser speckle imaging signal $LSI_{\lambda 1}$ (t) can be obtained.

The system shown in FIG. 12, according to an aspect of the present invention, comprises a coherent light source 16 comprising a first laser source 16a and a second laser source 16b that illuminate the tissue region of the subject with coherent light at the first and at the second wavelength λ1, λ2. The detector 18 can again be a camera such as a CCD camera or a CMOS camera. However, based on the output of the camera, it is now possible to obtain a first laser speckle imaging signal $LSI_{\lambda 1}$ (t) as the first flow signal indicative of a flow of lights scattering particles within the tissue region of the subject at the first wavelength, and a second laser speckle imaging signal $LSI_{\lambda 2}$ (t) as the second flow signal indicative of a flow of light scattering particles within the tissue region of the subject at the second wavelength. Furthermore, a first PPG signal $PPG_{\lambda 1}$ (t) indicative of an absorption of light within the tissue region of the subject at the first wavelength λ1 and a second PPG signal $PPG_{\lambda 2}$ (t) indicative of an absorption of light within the tissue region of the subject at the second wavelength λ2 can be obtained. Hence, such a dual wavelength setup can provide PPG and LSI signals from which PPG and flow signal modulation depths can be derived for blood oxygen saturation measurement with improved accuracy.

FIGS. 13A to 14B illustrate the scenario of blood oxygen saturation measurement with equal penetration depths. A PPG signal amplitude is proportional to $$PPG_\lambda \sim \mu_a(\lambda) \int I_\lambda(z) P(z) dz, \qquad (7)$$

wherein $\mu_a$ (λ) is the wavelength dependent absorption coefficient, I(z) denotes a relative contribution to detected intensity and P (z) denotes pulsatility versus skin depth z. However, as indicated in FIG. 6C and FIG. 7C respectively, an actual profile of the pulsatility as a function of depth (z), P (z) is generally unknown. The consequence of having different pulsatility profiles is not very dramatic for conventional transmission-based contact pulse oximeters, where $I_{\lambda 1}$ (z)≈$I_{\lambda 2}$ (z). In this case, the ratio of the red and infrared PPG amplitude depends mostly on $\mu_a$ (λ) and SpO2 can be estimated with reasonable accuracy. This scenario is indicated in FIG. 13A to FIG. 14B.

Figures 13A, 13B, 13C:
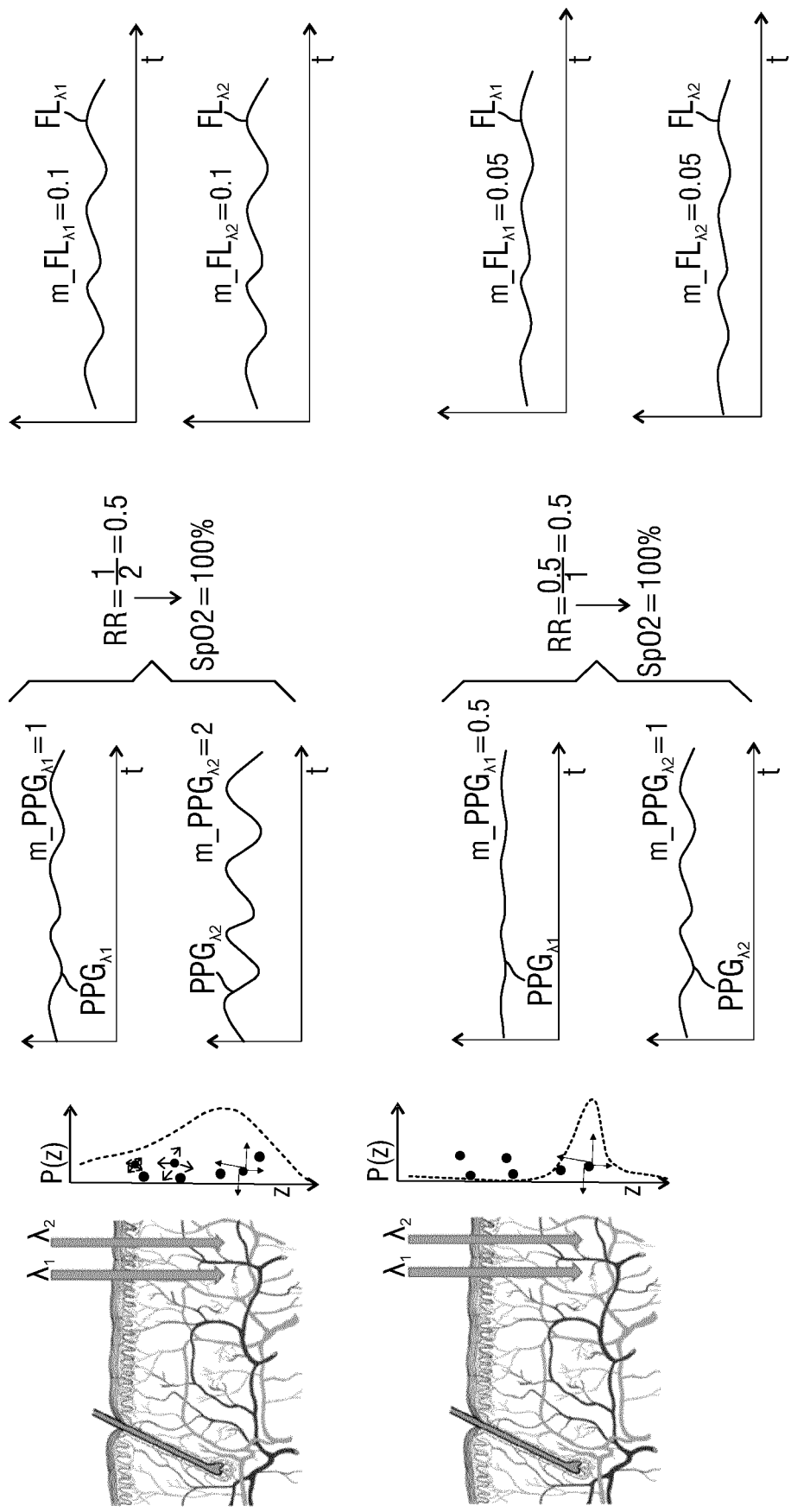
FIG. 13A shows two examples of light at a first wavelength and at a second wavelength having equal penetration depths but different vascular pulsatility profiles, as indicated by the insets on the right of the graphs in FIG. 13A, respectively.
FIG. 13B shows diagrams of exemplary PPG signals at the first and at the second wavelength for the first vascular pulsatility as indicated in FIG. 13A (upper graphs) and the second vascular pulsatility profile as indicated in FIG. 13A (lower graphs)
FIG. 13C shows diagrams of the corresponding flow signals at the first and at the second wavelength for the first vascular pulsatility profile as indicated in FIG. 13A (upper graphs) and the second vascular pulsatility profile as indicated in FIG. 13A (lower graphs)

As shown in FIG. 13A, the radiation at the first wavelength λ1 and at the second wavelength λ2 penetrate the tissue to the same extent. Hence, the assumption that the first and the second wavelength probe the same tissue depth is not violated. Thus, even assuming a different vascular pulsatility as indicated by the dashed curve P(z) in the insets on the right sides of the top and bottom graphs in FIG. 13A, the different vascular pulsatility profile does not substantially affect the ratio of ratios of the PPG amplitudes $m\_PPG_{\lambda 1}$ and $m\_PPG_{\lambda 2}$. Hence, in this case, the unknown pulsatility profile may not affect the SpO2 determination based on the PPG signals $PPG_{\lambda 1}$ and $PPG_{\lambda 2}$ as shown in FIG. 13B. Correspondingly, as shown in FIG. 13C, the flow signals at the first and at the second wavelength $FL_{\lambda 1}$ and $FL_{\lambda 2}$ also show a same modulation depth (AC/DC) given by $m\_FL_{\lambda 1}$ and $m\_FL_{\lambda 2}$, respectively.

Figures 14A, 14B:
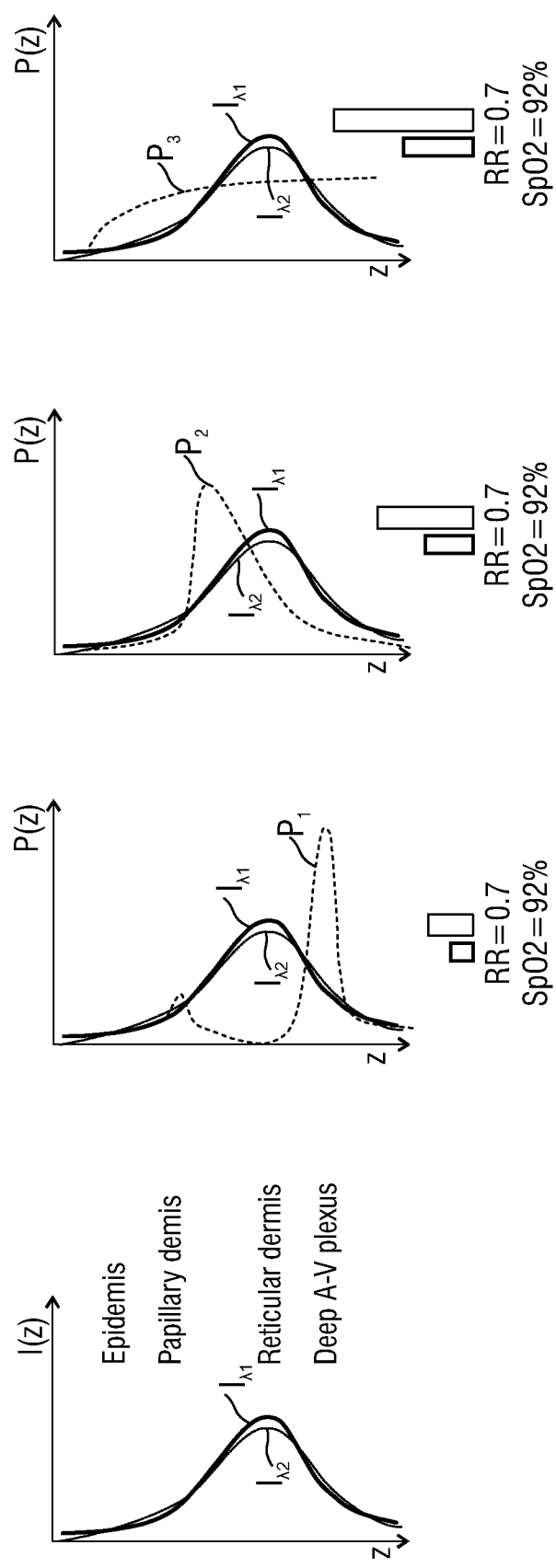
FIG. 14A shows a diagram of a relative contribution to the detected intensity at the first wavelength and at the second wavelength versus skin depth for a transmission-based measurement as shown in FIG. 6A.
FIG. 14B shows diagrams of three exemplary different pulsatility profiles in conjunction with the relative contribution to the detected intensity of FIG. 14A as well as a resulting ratio of ratios as indicated at the bottom.

FIG. 14A shows a graph of the relative contribution to detected intensity $I_\lambda(z)$ versus skin depth z. The curves $I_{\lambda 1}(z)$ and $I_{\lambda 2}(z)$ are approximately similar at the first wavelength and at the second wavelength. In FIG. 14B the impact of three different pulsatility profiles P1, P2 and P3 as indicated by the dashed curve is shown. As can be seen, the ratio of ratios is not substantially affected and leads to the correct blood oxygen saturation value, here 92%.

Turning now to FIG. 15A to 16B the variation of pulsatility profile with depth can have significantly more impact for a reflectance-based or remote blood oxygen saturation measurement. Substantially different penetration depths for the first and the second wavelength may occur. Hence, the PPG amplitude at the first and at the second wavelength as given by the formula above is now not only affected by the blood absorption coefficient $\mu_a(\lambda)$ but also depends on the wavelength-dependent relative penetration depths $I_\lambda(z)$ and the actual pulsatility profile P(z).

Penetration depths can depend on scattering and absorption. While infrared light scatters slightly less than red, it is not safe to conclude that infrared does typically penetrate slightly deeper than red. This is because HbO2 absorbs the light significantly better at infrared than at red, which has the opposite effect on penetration depth. And, for Hb this is slightly less true, compared to HbO2. Thus, a priori it is not clear which wavelength penetrates deeper. In fact, this can also change dynamically depending on venous pooling, and/or a changed saturation of the venous blood and/or opening and closing of shunts, e.g., due to centralization of a patient. Such physiological effects would impact both P(z) and Ia (z).

For example, when the skin regulates more blood towards the upper layer, it reduces the interrogation depth of both the red and infrared light, but extensively more for the infrared light, so disproportionally more than for the red light, due to its higher absorption coefficient. Thus, the infrared PPG signal amplitude may be reduced to a greater extent than the red PPG signal amplitude, which would then lead to an underestimation of SpO2.

FIG. 15A illustrates the case where light at a first wavelength λ1 and at a second wavelength λ2 shows a different penetration depth as indicated by the vertical arrows. Furthermore, the upper and the lower graphs in FIG. 15A show a different vascular pulsatility profile P(z) in the insets. In consequence, as shown in FIG. 15B, the PPG signals at the first wavelength $PPG_{\lambda 1}$ and at the second wavelength $PPG_{\lambda 2}$ will experience a different modulation $m\_PPG_{\lambda 1}$ and $m\_PPG_{\lambda 2}$. For example, the infrared light may penetrate less deep than red light. This, combined with a non-homogeneous vascular pulsatility profile can give erroneous SpO2 estimates both in the upper and the lower graphs in FIG. 15B. The accurate SpO2 value would have been 100% as shown in the previous FIG. 13B. This error depends on the pulsatility profile shown in the insets in the upper and lower graphs of FIG. 15A. In the lower graph, the upper tissue layers have less vascular pulsatility compared to the upper graph in FIG. 15A and the infrared PPG amplitude at the second wavelength λ2 can be reduced more extensively than the red PPG amplitude at the first wavelength λ1. This can in turn lead to an underestimation of SpO2.

It has been found that this error can be detected by looking at the differences in the flow signals acquired at the same wavelengths used for the PPG signals. For example speckle contrast modulation depths at the first and at the second wavelengths can be evaluated. If penetration depths of, for example, the red and infrared were equal, the infrared/red ratio of the speckle signal would be 1. However, if the probed pulsatile tissue layers differ, the flow signals at the first wavelength $FL_{\lambda 1}$ and at the second wavelength $FL_{\lambda 2}$ will experience a different modulation $m\_FL_{\lambda 1}$ and $m\_FL_{\lambda 2}$, as shown in FIG. 15C. In the given example, the LSI modulation depths indicate that red indeed sees more pulsatile layers than infrared. Hence, a modulation of the first flow signal at the first, red wavelength $m\_FL_{\lambda 1}$ is higher than a modulation of the second flow signal at the second, infrared wavelength $m\_FL_{\lambda 2}$.

Figure 16B:
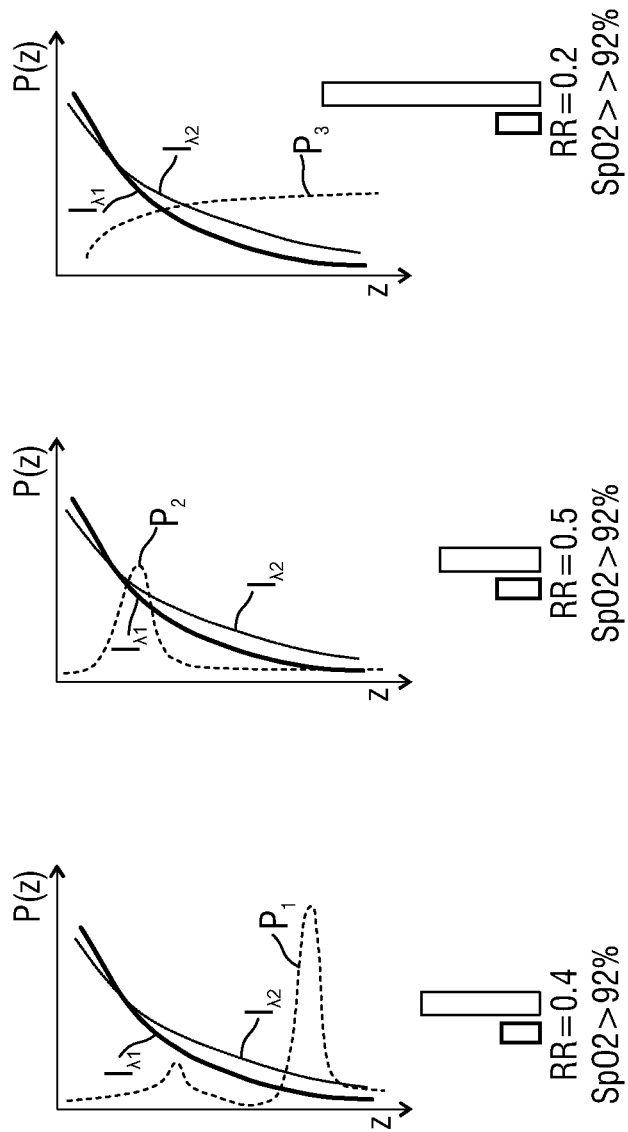
FIG. 16B shows diagrams of three exemplary different pulsatility profiles in conjunction with the relative contribution to the detected intensity of FIG. 16A as well as a resulting ratio of ratios as indicated at the bottom.
Figure 16A:
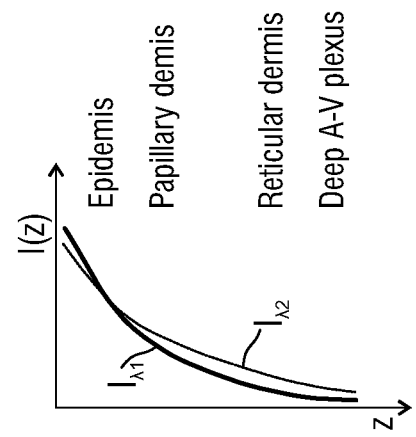
FIG. 16A shows a diagram of a relative contribution to the detected intensity at the first wavelength and at the second wavelength versus skin depth for a reflectance-based measurement as shown in FIG. 7A.

FIG. 16A shows a relative contribution to the detected intensity $I_\lambda(z)$ versus skin depth z at the first wavelength λ1 and at the second wavelength λ2. For a reflectance-based measurement, the contribution can be approximated by a wavelength-dependent exponential decay function. For example, red and infrared light may experience different penetration depths in a remote, camera-based setup, which can have non-linear consequences for the measured PPG signal at both wavelengths and their ratio, depending on the pulsatility profile.

In FIG. 16B this is exemplarily indicated for three different pulsatility profiles P1, P2, and P3 leading to an erroneous ratio of ratios of the first PPG signal and the second PPG signal on which the SpO2 estimation is based. In the shown example, this leads to an overestimation of SpO2. An important factor can be attributed to the gradually decreasing pulsatility as one comes closer to the surface or as arterioles come from beneath and branch into capillaries and thereby show reduced pulsatility.

With the solution proposed herein, this impact can be reduced. It has been found that the modulation depths of the flow signals at a first wavelength and at the second wavelength can be seen as a 'color blind', measure of the pulsatility such that it can be used to scale the PPG amplitudes (AC/DC) using the flow signal amplitudes (AC/DC).

In a first step, a conventional PPG ratio of ratios can be determined by calculating $$RR_{PPG} = PPG \frac{AC_{\lambda 1}/DC_{\lambda 1}}{AC_{\lambda 2}/DC_{\lambda 2}} = \frac{m\_PPG_{\lambda 1}}{m\_PPG_{\lambda 2}} \quad (8)$$

Correspondingly, a ratio of ratios can be determined for the flow signals by $$RR_{FL} = FL \frac{AC_{\lambda 1}/DC_{\lambda 1}}{AC_{\lambda 2}/DC_{\lambda 2}} = \frac{m\_FL_{\lambda 1}}{m\_FL_{\lambda 2}} \quad (9)$$

Based thereon, a corrected ratio of ratios can be determined which then can form the basis for SpO2 calculation by $$RR_{corrected} = RR_{PPG}/RR_{FL} \quad (10)$$

Based thereon, a the blood oxygen saturation SpO2 can be determined, for example using a look-up table or a calibration curve such as $$SpO2 = C_1 - C_2 \cdot RR_{corrected} \quad (11)$$

For the scenario shown in the upper graph of FIG. 15A to FIG. 15C, the corrected ratio of ratios can thus be determined by $$RR_{corrected} = \frac{0.9/1.6}{0.9/0.8} = 0.5 \quad (12)$$
$$\rightarrow SpO2 = 100\%$$

Correspondingly in the lower graphs of FIG. 15A to FIG. 15C, a corrected ratio of ratios can be determined by $$RR_{corrected} = \frac{0.8/1.2}{0.8/0.6} = 0.5 \quad (13)$$
$$\rightarrow SpO2 = 100\%$$

In the example shown above the PPG ratio of ratios has been scaled with the flow signal ratio of ratios. Of course, it is also possible to scale each PPG signal with its respective flow signal at the same wavelength. In particular when dealing with more than two wavelengths, the last scaling becomes more obvious. Hence, at each wavelength a correction can be applied in the form of $$m\_PPG_\lambda, corrected = m\_PPG_\lambda / m\_FL_\lambda \quad (14)$$

In a multiple-wavelength approach, the relative PPG amplitudes can be described as vector (5, 3, 2), or, as a normalized vector (0.81, 0.49, 0.32). The scaling of a PPG signal with the flow signal at the respective wavelengths can take place before or after normalization.

It shall be understood that an absolute modulation depth or a relative, i.e., normalized, modulation depth of the flow signal can be used. For example, an absolute modulation depth may increase due to an increased pulsatile component or a reduced DC component, for example due to a steady, non-pulsatile flow. In consequence, the modulation depths would change for both the wavelengths to the same degree and the correction of the PPG amplitudes by these different flow signals would still be correct since the same ratio applies. Hence, such a difference would not corrupt the proposed correction.

Figure 17A:
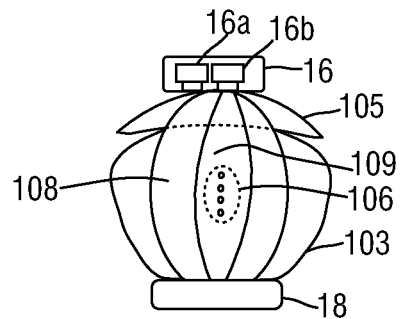
FIG. 17A shows a first cross-sectional view through a finger in a transverse plane including the volumes probed at a first wavelength and at a second wavelength.
Figure 17B:
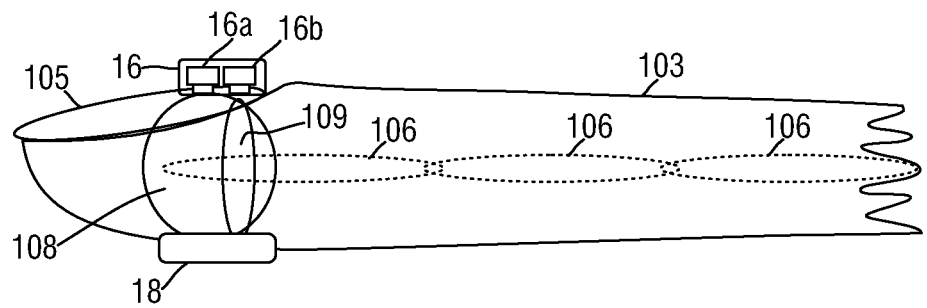
FIG. 17B shows a second cross-sectional view of the finger of FIG. 17A again including the different volumes probed at the first wavelength and at the second wavelength.

Turning now to FIG. 17A and FIG. 17B, this embodiment shows that the proposed solution can also be advantageous for a transmission-based measurement and not only for a reflectance-based remote measurement of blood oxygen saturation. FIG. 17A shows a cross-sectional view through a finger 103 of a subject similar to the embodiment shown in FIG. 3. The finger 103 further comprises a finger nail 105 and bones 106. The coherent light source 16 comprises a first laser diode 16a arranged to emit coherent light at a first wavelength through the finger 103 of the subject and a second laser diode 16b arranged to emit coherent light at a second wavelength through the finger 103 of the subject. A detector 18 acquires detection data over time by detecting radiation at the first and at the second wavelength received from said tissue region in response to the coherent light at the first wavelength and coherent light at the second wavelength being emitted towards the tissue region.

As illustrated in FIG. 17A and FIG. 17B, even for the transmission-based measurement, a different volume comprising different pulsatile tissue layers may be probed at the different wavelengths. A first volume 108 may be probed at the first wavelength λ1 and a second volume 109 may be probed at the second wavelength λ2. With the solution disclosed herein, this can be advantageously corrected.

For example, in FIG. 17A and FIG. 17B, red may be absorbed less than infrared, e.g. because most of the blood is well saturated. As a result, the probing volume 108 for red is much wider than the probing volume 109 for infrared. Only those infrared photons that travel in an almost straight line from source to detector have a chance of reaching the detector. Red photons have more freedom to scatter around in the pulsatile volume before arriving at the source since the attenuation is much weaker. It shall be understood that another example could also be construed in which the difference between wavelengths is turned around, i.e., infrared may be absorbed less than red. Furthermore, a bone 106 causes an obstruction in the light paths such that light has to go around. In the given example, infrared will be perturbed more by this obstruction than red. However, even without such an obstruction, it is likely that the different probing volumes cause slightly different modulation depths that are unrelated to the oxygen saturation of the blood in the pulsatile vessels. A correction based on flow signals can therefore also help to improve the reliability in transmission-based measurements.

As system for use in a scenario as shown in FIG. 17A and FIG. 17B can be implemented as, for example, described above with reference to FIG. 3 and FIG. 4. A single photodiode can be as the detector 18. In this case, the first and second flow signals can be determined based on a laser Doppler technique. It shall be understood that also for the aforementioned camera-based case, based on laser speckle imaging and camera-based PPG, both the flow and PPG signals can result in signals averaged over a region of interest. Hence, the signals can essentially be condensed down to point measurements without spatial x or y information, only having temporal variation, similar to a signal derived using a single (non-image) detector. The principle of scaling PPG signals with flow signals at the respective wavelengths can thus also be applied for non-image signals.

Figure 18:
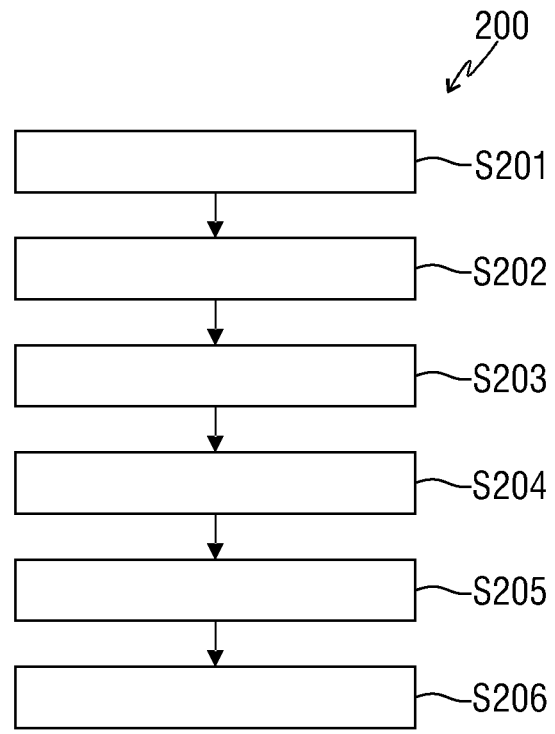
FIG. 18 shows a flow chart of a method according to an aspect of the present invention.

A flow chart of a method 200 according to an aspect of the present invention is illustrated in FIG. 18. In a first step S201 first detection data of a tissue region of a subject are obtained (i.e., received or retrieved). In a second step S202 second detection data of the tissue region of the subject is obtained (i.e., received or retrieved). Optionally, the second detection data can be obtained and used as the first detection data. Hence, the same detection data can be used. In a third step S203 a first PPG signal and a second PPG signal are derived from said first detection data. In a fourth step S204 a first flow signal and a second flow signal are derived from said second detection data. It should be noted that the fourth step S204 may also be carried out before or simultaneously to the third step S203. In a fifth step S205 said PPG signals can be corrected based on said flow signals and/or a feedback signal can be provided based on a comparison of the first and the second flow signals. In an optional further step S206 subsequent to correcting said PPG signals, a blood oxygen saturation value of the subject can be determined based on the corrected PPG signals.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A processing device for use in blood oxygen saturation measurement of a subject, the processing device comprising:
an input for receiving first and second detection data of a tissue region of the subject, said first detection data being data acquired over time by detecting radiation at a first wavelength and at a second wavelength received from said tissue region; said second detection data being data acquired over time by detecting radiation at the first wavelength and at the second wavelength received from said tissue region in response to coherent light at the first wavelength and coherent light at the second wavelength being emitted towards the tissue region; and
a processor for,
(a) deriving, from said first detection data, a first PPG signal indicative of an absorption of light within the tissue region at the first wavelength, and a second PPG signal indicative of an absorption of light within the tissue region at the second wavelength;
(b) deriving, from said second detection data, a first flow signal indicative of a flow of light scattering particles within the tissue region probed at the first wavelength, and a second flow signal indicative of a flow of light scattering particles within the tissue region probed at the second wavelength; and
(c) providing a feedback signal based on a comparison of the first and second flow signals, said feedback signal being indicative of a quality of the PPG signals and derived from a mismatch between the first flow signal at the first wavelength and the second flow signal at the second wavelength.

2. The processing device as claimed in claim 1, wherein the processor is further configured to correct said PPG signals based on said flow signals.

3. The processing device as claimed in claim 2, wherein the processor is further configured to provide an output indicative of a blood oxygen saturation of the subject based on said corrected PPG signals.

4. The processing device as claimed in claim 2, wherein the processor is configured to correct the first and the second PPG signal based on a temporal modulation of the first and the second flow signal at the first wavelength and the second wavelength.

5. The processing device as claimed in claim 2, wherein the processor is configured to correct the PPG signals by scaling amplitudes of the first and the second PPG signal at the first wavelength and the second wavelength based on amplitudes of the first and the second flow signal at the first wavelength and the second wavelength.

6. The processing device as claimed in claim 1, wherein the processor is configured to determine the first and the second PPG signal based on an average of the detected radiation at the first wavelength and at the second wavelength.

7. The processing device as claimed in claim 1, wherein the processor is configured to derive the first and second flow signal based on at least one of laser Doppler technique or laser speckle technique.

8. The processing device as claimed in claim 1, wherein the processor is configured to determine the first and the second flow signal based on a standard deviation of the detected radiation at the first wavelength and at the second wavelength.

9. The processing device as claimed in claim 1, wherein the processor is configured to determine the first and the second flow signals based on a speckle contrast at the first wavelength and the second wavelength.

10. The processing device as claimed in claim 1, wherein the processor is configured to determine a ratio of ratios of the PPG signals and to correct said ratio of ratios of the PPG signals based on a ratio of ratios of the flow signals.

11. A system for use in blood oxygen saturation measurement of a subject, the system comprising;
a coherent light source arranged to emit coherent light at a first wavelength and at a second wavelength towards a tissue region of the subject
a detector for acquiring first and second detection data of the tissue region of the subject, said first detection data being acquired over time by detecting radiation at a first wavelength and at a second wavelength received from said tissue region; said second detection data being acquired over time by detecting radiation at the first wavelength and at the second wavelength received from said tissue region in response to the coherent light at the first wavelength and coherent light at the second wavelength being emitted towards the tissue region; and
the processing device as claimed in claim 1 for processing said first and said second detection data of the tissue region of the subject.

12. The system as claimed in claim 11, arranged as a remote PPG system.

13. The system as claimed in claim 12, wherein the remote PPG system comprises a camera.

14. A method for use in blood oxygen saturation measurement of a subject, the method comprising the steps of:
receiving first and second detection data of a tissue region of the subject, said first detection data being data acquired over time by detecting radiation at a first wavelength and at a second wavelength received from said tissue region; said second detection data being data acquired over time by detecting radiation at the first wavelength and at the second wavelength received from said tissue region in response to coherent light at the first wavelength and coherent light at the second wavelength being emitted towards the tissue region;
deriving, from said first detection data, a first PPG signal indicative of an absorption of light within the tissue region at the first wavelength, and a second PPG signal indicative of an absorption of light within the tissue region at the second wavelength;
deriving, from said second detection data, a first flow signal indicative of a flow of light scattering particles within the tissue region probed at the first wavelength, and a second flow signal indicative of a flow of light scattering particles within the tissue region probed at the second wavelength; and
at least one of correcting said PPG signals based on said flow signals or providing a feedback signal based on a comparison of the first and second flow signals.

15. A non-transitory computer-readable medium that stores therein a computer program product, which, when executed on a processor, causes the following steps to be performed:
receiving first and second detection data of a tissue region of a subject, said first detection data being data acquired over time by detecting radiation at a first wavelength and at a second wavelength revived from said tissue region, said second detection data being data acquired over time by detecting radiation at the first wavelength and at the second wavelength received from said tissue region in response to coherent light at the first wavelength and coherent light at the second wavelength being emitted towards the tissue region;

deriving, from said first detection data, a first PPG signal indicative of an absorption of light within the tissue region at the first wavelength, and a second PPG signal indicative of an absorption of light within the tissue region at the second wavelength;

deriving, from said second detection data, a first flow signal indicative of a flow of light scattering particles within the tissue region probed at the first wavelength, and a second flow signal indicative of a flow of light scattering particles within the tissue region probed at the second wavelength; and at least one of correcting said PPG signals based on said flow signals or providing a feedback signal based on a comparison of the first and second flow signals.

* * * * *